US005672697A

United States Patent [19]
Buhr et al.

[11] Patent Number: 5,672,697
[45] Date of Patent: Sep. 30, 1997

[54] NUCLEOSIDE 5'-METHYLENE PHOSPHONATES

[75] Inventors: Chris Buhr, Daly City; Mark Matteucci, Burlingame; Norbert W. Bischofberger, San Carlos; Brian Froehler, Belmont, all of Calif.

[73] Assignee: Gilead Sciences, Inc., Foster City, Calif.

[21] Appl. No.: 652,978

[22] Filed: Feb. 8, 1991

[51] Int. Cl.$^6$ ...................... C07H 19/073; C07H 19/173
[52] U.S. Cl. ........................................... 536/26.7; 536/26.8
[58] Field of Search .......................... 536/27–29, 28.2, 536/27.81, 28.5, 28.53, 28.55, 26.7, 26.8; 514/46, 47–48, 51

[56] References Cited

U.S. PATENT DOCUMENTS

| | | | |
|---|---|---|---|
| 3,446,793 | 5/1969 | Jones et al. | 536/26.13 |
| 3,524,846 | 8/1970 | Moffatt et al. | 536/26.71 |
| 3,560,478 | 2/1971 | Myers | 536/26.2 |
| 3,662,031 | 5/1972 | Moffatt et al. | |
| 3,736,314 | 5/1973 | Jones et al. | 536/26.7 |
| 3,878,194 | 4/1975 | Moffatt et al. | |
| 4,291,024 | 9/1981 | Turcotte | 536/26.2 |
| 4,689,407 | 8/1987 | Morr et al. | |
| 4,757,055 | 7/1988 | Miller et al. | |
| 4,918,179 | 4/1990 | Watanabe et al. | 536/24 |
| 5,043,437 | 8/1991 | Khorlin et al. | 536/29 |

FOREIGN PATENT DOCUMENTS

| | | |
|---|---|---|
| A1 0 263 740 | 4/1988 | European Pat. Off. . |
| A3 0 357 571 | 3/1990 | European Pat. Off. . |
| 0417999 | 3/1991 | European Pat. Off. . |
| 2009 834 | 9/1970 | Germany . |
| 1 243 213 | 8/1971 | United Kingdom . |
| WO84/04748 | 12/1984 | WIPO . |
| WO 89/12061 | 12/1989 | WIPO . |

OTHER PUBLICATIONS

Almer et al., "Synthesis of a phosphonomethyl analogue of 3'-deoxy-3'-fluorothymidine," *Acta Chemica Scandinavia* 45(7):766–767 (1991) Month No Available.

Buhr et al, "Synthesis and Antiviral Activity of 5'-Methylene-Phosphonate Nucleosides," *Collect Czech Chem Commun* 58:102–104 (1993) Month Not Available.

Uhlmann et al., *Chemical Reviews* (1990) 90:543–584 Month not available.

Frick et al., Meeting Abstract, Conference on Nucleic Acid Therapeutics, Jan. 13–17, 1991, Clearwater Beach, Florida, p. 63 Month Not Available.

Ikehara et al., *Heterocycles* (1984) 21:75–90 Month not available.

Kim et al, "Acyclic Purine Phosphonate Analogues as Antiviral Agents. Synthesis and Structure—Activity Relationships", *J. Med. Chem.*, vol. 33, (1990), pp. 1207–1213 Month Not Available.

Stein, et al., "Oligodeoxynucleotides as Inhibitors of Gene Expression: A Review," *Cancer Res.*, 48:2659–2688 (1988) Month Not Available.

van der Krol, et al., "Modulation of Eukaryotic Gene Expression by Complementary RNA or DNA Sequences," *BioTechniques*, 6:958–976 (1988) Month Not Available.

Weintraub, H.M., "Antisense RNA and DNA," *Scientific American*, 40–46 (January 1990) Month Not Available.

Goodchild, J., "Inhibition of Gene Expression by Oligonucleotides," *Oligodeoxynucleotides: Antisense Inhibitors of Gene Expression*, chapter 3 (J.S. Cohen, ed.) 1989, CRC Press, Boca Raton, Florida Month Not Available.

Dervan, P.B., "Oligonucleotide Recognition of Double–helical DNA by Triple–helix Formation," *Oligodeoxynucleotides: Antisense Inhibitors of Gene Expression*,chapter 9 (J.S. Cohen, ed.) 1989, CRC Press, Boca Raton, Florida Month Not Available.

Dervan, P.B., "Sequence Specific Recognition of Double Helical DNA. A Synthetic Approach," *Nucleic Acids and Molecular Biology*,vol. 2, pp. 49–64 (F. Eckstein and D.M.J. Lilley, eds.) 1988, Springer–Verlag, Berlin Month Not Available.

Zon, G., "Oligonucleotide Analogues as Potential Chemotherapeutic Agents," *Pharmaceutical Res.* 5:539–549 (1988) Month Not Available.

Stein et al., "Phosphorothioate Oligodeoxynucleotide Analogues," *Oligodeoxynucleotides: Antisense Inhibitors of Gene Expression*, chapter 5 (J.S. Cohen, ed.) 1989, CRC Press, Boca Raton, Florida Month Not Available.

Caruthers, M.H., "Synthesis of Oligonucleotides and Oligonucleotide Analogues," *Oligodeoxynucleotides: Antisense Inhibitors of Gene Expression*, chapter 1, (J.S. Cohen, ed.) 1989, CRC Press, Boca Raton, Florida. Month Not Available.

Grandas, et al., "Synthesis of Deoxycytidine Oligomers Containing Phosphorodithioate Linkages," *Tetrahedron Lett.* 30(5):543–546 (1989) Month Not Available.

Brill, et al., "Synthesis of Oligodeoxynucleoside Phosphorodithioates via Thioamidites," *J. Amer. Chem. Soc.* 111:2321–2322 (1989) Month Not Available.

Caruthers, et al., "Synthesis and Biological Studies with Dithioate DNA," 9th International Round Table: Nucleosides, Nucleotides, and their Biological Applications (Jul. 30–Aug. 3, 1990) Uppsala, Sweden Month Not Available.

Miller, P.S., "Non–ionic Antisense Oligonucleotides," *Oligodeoxynucleotides: Antisense Inhibitors of Gene Expression*, chapter 4 (J.S. Cohen, ed.) 1989, CRC Press, Boca Raton, Florida Month Not Available.

Engel, R., "Phosphonates as Analogues of Natural Phosphates," *Chem. Rev.* 77:349–367 (1977) Month Not Available.

(List continued on next page.)

*Primary Examiner*—Gary L. Kunz
*Attorney, Agent, or Firm*—Daryl D. Muenchau

[57] ABSTRACT

Novel oligonucleotides analogs and nucleoside analogs as well as methods for their synthesis are described. The oligonucleotides are useful in diagnostic and therapeutic applications. The oligonucleotides are stable to nuclease degradation.

8 Claims, No Drawings

OTHER PUBLICATIONS

Mikhailov, et al., "Use of 5-Deoxy-ribo-Hexofuranose Derivatives for the Preparation of 5'-Nucleotide Phosphonates and Homoribonucleosides," *Collect. Czech. Chem. Commun.*, 54:1055–1067 (1989) Month Not Available.

Martin, et al., "Synthesis of 4'-Hydroxymethyl)Guanosine and a Phosphonate Analogue of Guanylic Acid," *Nucleosides and Nucleotides*, 7(3):365–374 (1988) Month Not Available.

Hampton, et al., "Synthesis of Homoadenosine-6'-phosphonic Acid and Studies of Its Substrate and Inhibitor Properties with Adenosine Monophosphate Utilizing Enzymes," *BioChemistry*, 12:1730–1736 (1973) Month Not Available.

Hampton, et al., "Synthesis of 6'-Cyano-6'-deoxyhomoadenosine-6'-phosphonic Acid and Its Phosphoryl and Pyrophosphoryl Anhydrides and Studies of Their Interactions with Adenine Nucleotide Utilizing Enzymes," *Amer. Chem. Soc.*, 95(13):4404–4414 (1973) Month Not Available.

Montgomery, et al., "The Use of the Wittig Reaction in the Modification of Purine Nucleosides," *J. Het. Chem.*, 11:211–218 (1974) Month not available.

Hampton, et al., "Design of Substrate–Site–Directed Inhibitors of Adenylate Kinase and Hexokinase. Effect of Substrate Substituents on Affinity for the Adenine Nucleotide Sites," *J. Med. Chem.*, 19:1371–1377 (1976) Month Not Available.

Kappler, et al., "Isozyme–Specific Enzyme Inhibitors. 10. Adenosine 5'-Triphosate Derivatives as Substrates or Inhibitors of Methionine Adenosyltransferases of Rat Normal and Hepatome Tissues," *J. Med. Chem.*, 29:318–322 (1986) Month Not Available.

Fuertes, et al., "Synthesis and Enzymatic Activity of 1,2,4-Triazole–3–carboxamide 6'-Deoxyhomoribonucleoside–6'-phosphonic Acid and Related Compounds," *J. Med. Chem.*, 17(6):642–645 (1974) Month Not Available.

Marquez, et al., "Thiazole-4-carboxamide Adenine Dinucleotide (TAD). Analogues Stable to Phosphodiesterase Hydrolysis," *J. Med. Chem.*, 29:1726–1731 (1986) Month Not Available.

Albrecht, et al., "Homonucleoside Phosphonic Acids," *Tetrahedron*, 40(1):79–85 (1984) Month Not Available.

Mazur, A., et al., "Isosteres of Natural Phosphates. 11. Synthesis of a Phosphonic Acid Analogue of an Oligonucleotide," *Tetrahedron*, 40(20):3949–3956 (1984) Month Not Available.

Barton, et al., "Stereoselectivity in Radical Reactions of 2'-Deoxynucleosides. A Synthesis of an Isostere of 3'-azido-3'-deoxythymidine-5'-monophosphate," *Tetrahedron Lett.*, 30(37):4969–4972 (1989) Month Not Available.

Tanaka, et al., "Cleavage of a Nucleosidic Oxetane with Carbanions: Synthesis of a Highly Promising Candidate for Anti–HIV Agents—A Phosphonate Isostere of ACT 5'-Phosphate," *Tetrahedron Lett.*, 30(19):2567–2570 (1989) Month Not Available.

Montgomery, et al., "Phosphonate Analogue of 2'-Deoxy-5-fluorouridylic Acid," *J. Med. Chem.*, 22(1):109–111 (1979) Month Not Available.

Griffin, et el., "Nuclear Magnetic Resonance Studies of a Ribonuclease–Dinucleoside Phosphonate Complex and Their Implications for the Mechanism of the Enzyme," *Annals New York Academy of Sciences*, 222:693–708 (1978) Month Not Available.

Kaplan, et al., "DNA Synthesis on Solid Supports and Automation," *Synthesis and Applications of DNA and RNA*, chapter 2 (S.A. Narang, ed.) 1987, Academic Press, Orlando, Florida Month Not Available.

Crockett, G.C., "The Chemical Synthesis of DNA," *Aldrichimica Acta*, 16:47–55 (1983) Month Not Available.

Agarwal, et al., "Chemical Synthesis of Polynucleotides," *Angew. Chem. internat. Edit.*, 11(6):451–459 (1972) Month Not Available.

Sproat, et al., "Solid–phase Synthesis of Oligodeoxyribonucleotides by the Phosphotriester Method," *Oligonucleotide Synthesis: A Practical Approach*, chapter 4 (M.J. Gait, ed.) 1984, IRL Press, Oxford, England Month Not Available.

Prisbe, et al., "Synthesis and Antiherpes Virus Activity of Phosphate and Phosphonate Derivatives of 9–[(1, 3–Dihydroxy–2–propoxy)methyl]guanine," *J. Med. Chem.*, 29:671–675 (1986) Month Not Available.

Duke, et al., "In vitro and in vivo activities of phosphate derivatives of 9–(1,3–dihydroxy–2–propooxymethyl)–guanine against cytomegaloviruses," *Antiviral Research*, 6:299–308 (1986) Month Not Available.

Reist, et al., "Synthesis of Phosphonic Acid Analogs of Acyclovir (ACV) and Ganciclovir (DHPG)," *Nucleosides and Nucleotides*, 8:919–922 (1989) Month Not Available.

Sidwell, et al., "Effect of Phosphonic Acid Analogs of Acyclovir and Ganciclovir on in vitro cytomegalovirus infections," *Nucleosides and Nucleotides*, 8:833–836 (1989) Month Not Available.

Still, et al., "Rapid Chromatographic Technique for Preparative Separations with Moderate Resolution," *J.Org. Chem.*, 43:2923–2925 (1978) Month Not Available.

Jones, R., *Oligonucleotide Synthesis: A Practical Approach*, chapter 3, pp. 25–27 (M.J. Gait, ed.) 1984, IRL Press Limited, Oxford, England Month Not Available.

Jones, R., "Protection of the 5'-Hydroxyl Group as a 4,4'-Dimethoxytrityl Ether," *Oligonucleotide Synthesis: A Practical Approach*, chapter 4.1, pp. 27–28 (M.J. Gait, ed.) 1984, IRL Press Limited, Oxford, England Month Not Available.

Jones, et al., "A New Stable Wittig Reagent Suitable for the Synthesis of α, β–Unsaturated Phosphonates," *Tetrahedron Lett.*, 55:5731–34 (1968) Month Not Available.

Cusack, et al., "2,4,6–Tri–Isopropylbenzenesulphonyl Hydrazide: A Convenient Source of Di–imide," *Tetrahedron*, 32:2157–62 (1976) Month Not Available.

ElAmin, et al., "Removal of Benzyl–type Protecting Groups from Peptides by Catalytic Transfer Hydrogenation with Formic Acid," *J. Org. Chem.*, 44(19):3442–3444 (1979) Month Not Available.

Chu, et al., "Nucleosides. CXXXV. Synthesis of Some 9–(2–Deoxy–2–fluoro–β–D–arabinofuranosyl)–9H–purines and Their Biological Activities," *Chem. Pharm. Bull.*, 37(2):336–339 (1989) Month Not Available.

Watanabe, et al., "Nucleosides. 110. Synthesis and Antiherpes Virus Activity of Some 2'-Fluoro-2'deoxyarabinofuranosylpyrimidine Nucleosides," *J. Med. Chem.*, 22(1):21–24 (1979) Month Not Available.

Tann, et al. "Fluorocarbohydrates in Synthesis. An Efficient Synthesis of 1-(2-Deoxy-2-fluoro-β-D-arabinofuranosyl)-5-iodouracil (β-FIAU) and 1-(2-Deoxy-2-fluoro-β-D-arabinofuranosyl)thymine (β-FMAU)," J. Org. Chem., 50:3644–3647 (1985) Month Not Available.

Howell, et al., "Antiviral Nucleosides. A Stereospecific, Total Synthesis of 2'-Fluoro-2'-deoxy-β-D-arabinofuranosyl Nucleosides," J. Org. Chem., 53:85–88 (1988) Month Not Available.

van de Sande, et al., "Parallel Stranded DNA," Science, 241:551–557 (1988) Month Not Available.

Atkinson, et al., "Solid-phase Synthesis of Oligodeoxyribonucleotides by the Phosphite-triester Method," Oligonucleotide Synthesis: A Practical Approach, chapter 3, (M.J. Gait, ed.) 1984, IRL Press Limited, Oxford, England Month Not Available.

E. de Vries, et al, Mol. Biochem. Parasitol., 1991, 47, 43–50. Month Not Available.

Antineoplastic Agents, pp. 127–165, (W.A. Remers, ed.) 1984, Wiley & Sons, New York. Month Not Available.

Sterzycki, et al., "Synthesis and Anti-HIV Activity of Several 2'-Fluore-Containing Pyrimidine Nucleosides," J. Med. Chem., 33:2150–2157 (1990) Month Not Available.

Padyukova et al., Tetrahedron Letters (1987) 28(31):3623–3626 Month Not Available.

Kappler et al., J. Med. Chem. (1986)29:1030–1038 Month Not Available.

Albrecht et al., (1970)J. Am. Chem. Soc. 92:5511–5513 Month Not Available.

Breaker et al., (1990) Nucleic Acids Res. 18:3085–3086 Month Not Available.

Cozzone et al., (1983) FEBS Lett. 155:55–60 Month Not Available.

Jones et al., (1968) J. Amer. Chem. Soc. 90:5337–5338.

Jones et al., (1970) J. Amer. Chem. Soc. 92:5510–5511.

Akesson–Johansson et al., "Inhibition of Human Herpesvirus 6 Replication by 9-[4-Hydroxy-2-Hyrdroxymethyl)Butyl]Guanine (2HM-HBG) and Other Antiviral Compounds," Antimicro AG & Chemo 34(12):2417–2419 (Dec. 1990) Month Not Available.

Montgomery et al., "9-(2-Deoxy-2-fluoro-beta-D-arabinofuranosyl)guanine: A Metabolically Stable Cytotoxic Analogue of 2'-Deoxyguanosine," J Med Chem 29:2389–2392 (1986) Month Not Available.

Perlman et al., "Nucleosides. 133. Synthesis of 5-Alkenyl-1-(2-deoxy-2-fluoro-beta-D-arabinofuranosyl)cytosines and Related Pyrimidine Nucleosides as Potential Antiviral Agents," J Med Chem 28:741–748 (1985) Month Not Available.

Roizman, Bernard, "Herpesviridae: A Brief Introduction," Fields, Virology, 2nd ed. Chapter 64, pp. 1787–1793 (1990) Month Not Available.

Spector et al., "Conversion of 2,6-Diamino-9-(2-Hydroxyethoxymethyl)Purine to Acyclovir as Catalyzed by Adenosine Deaminase," Biochem Pharm 32(17):2505–2509 (1983) Month Not Available.

Su et al., "Nucleosides. 136. Synthesis and Antiviral Effects of Several 1-(2-Deoxy-2-fluoro-beta-D-arabinofuranosyl)- 5-alkyluracils. Some Structure–Activity Relationships," J Med Chem 29:151–154 (1986) Month not available.

Lin et al., "Prolonged Inhibitory Effect of 9-(1,3-Dihydroxy-2-Propoxymethyl)Guanine Against Replication of Epstein–Barr Virus," J Virol 50:50–55 (Apr. 1984).

Martin et al. J. Med. Chem. 33:2137–2145, 1990 Month Not Available.

Ranganathan, R. Tetrahedron Letters 15:1291–1294, 1977 Month Not Available.

Robins et al. J. Org. Chem. 39(11):1564–1570 Month Not Available.

Padyukova et al. Tetrahedron Letters 28:3623–3626, 1987 Month Not Available.

CA 107(25):228492a Balzarini et al. Mol. Pharm. 32(1):162–167, 1987 Month Not Available.

Martin et al. Chem. Abstr. vol. 109, p. 906, Abstr. No. 231447m, 1988; Nucleosides Nucleotides, 7(3):365–374, 1988 Month Not Available.

Webb et al. Nucl. Acid Res. 14(9):7661–7674, 1986.

Montgomery et al. J. Med. Chem. vol. 22, No. 1, pp. 109–111, 1979.

NUCLEOSIDE 5'-METHYLENE PHOSPHONATES

FIELD OF THE INVENTION

This invention relates to novel methylene phosphonate nucleosides which exhibit antiviral and antitumor activity and novel oligonucleotides derived from methylene phosphonate nucleoside monomers that have enhanced nuclease stability. The invention also relates to processes for preparing the novel compounds, their derivatives and oligonucleotides containing one or more 5' methylene phosphonate internucleotide linkages. The oligonucleotides are resistant to nuclease degradation and are useful for diagnostic and therapeutic applications.

BACKGROUND ART

Antisense and triple helix oligonucleotides are synthetic oligonucleotides which bind complementary nucleic adds (i.e. sense strand RNA or duplex DNA sequences) via hydrogen bonding, thereby inhibiting expression of these sequences. Therapeutic intervention at the nucleic acid level using oligonucleotides offers a number of advantages. Inhibition of gene expression is more efficient than inhibition of the protein encoded by the gene since transcription of a single DNA sequence gives rise to multiple copies of mRNA which, in turn, are translated into many protein molecules.

Oligonucleotides have been used to inhibit gene expression in a variety of systems. There are several reviews that discuss this topic.[1-4] In addition, the use of oligonucleotides in sequence-specific recognition of double stranded DNA[5,6] as well as potential chemotherapeutic agents,[7] has been reviewed.

An important feature of the antisense oligomeric probes is the design of the backbone of the administered oligomer. Specifically, the backbone should contain internucleoside linkages that are stable in vitro and should be structured such that the oligomer is resistant to endogenous nucleases, such as nucleases that attack the phosphodiester linkage.[8] At the same time, the oligomer must also retain its ability to hybridize to the target DNA or RNA. In order to ensure these properties, a number of modified oligonucleotides have been constructed which contain alternate internucleoside linkages. Several of these oligonucleotides are described in Uhlmann, E. and Peyman, A., *Chemical Reviews* (1990) 90:543–584. Among these are methylphosphonates (wherein one of the phosphorous-linked oxygens has been replaced by methyl); phosphorothioates[8,9] (wherein sulphur replaces one of these oxygens) and various amidates (wherein $NH_2$ or an organic amine derivative, such as morpholidates or piperazidates, replace an oxygen). These substitutions confer enhanced stability, for the most part, but suffer from the drawback that they result in a chiral phosphorous in the linkage, thus leading to the formation of $2^n$ diastereomers where n is the number of modified diester linkages in the oligomer. The presence of these multiple diastereomers considerably weakens the capability of the modified oligonucleotide to hybridize to target sequences. Some of these substitutions also retain the ability to support a negative charge and the presence of charged groups decreases the ability of the compounds to penetrate cell membranes. There are numerous other disadvantages associated with these modified linkages, depending on the precise nature of the linkage. Phosphorodithioate modified backbones have been made.[9,10] These modified oligonucleotides are nuclease resistant and are diastereomerically pure. However, these modifications further reduce the affinity of the oligonucleotide for its intended target.[10c] A variety of modified nonionic[11] oligonucleotides including methylphosphonate, phosphoroamidate, and phosphotriesters generally are either composed of a mixture of diastereomers, have a low affinity for intended targets, or both.

A deoxyoligonucleotide comprised from nucleotide monomers that contain a methylene (—$CH_2$—) group substituted for the 5'-oxygen may be resistant to nucleases, especially those that leave a 3'-phosphate moiety after cleavage of the internucleotidic bond. This results from the fact that the requisite P—C bond can not be cleaved under normal physiological conditions. Additionally, a single diastereomerically pure deoxyoligonucleotide could be prepared, as the internucleotide phosphorous linkages would be achiral. We refer to the nucleotides containing a methylene (—$CH_2$—) group substituted for the 5'-oxygen as 5'-methylene phosphonates.

The preparation of ribo (ie 2'-OH) 5'-methylene phosphonates is well documented in the literature.[12] Uridine,[13-15] adenosine,[13-15] and guanosine[16] 5'-methylene phosphonates have been prepared. A number of analogues of adenosine 5'-methylene phosphonate have been prepared.[17-23] In addition, ribavirin 5'-methylene phosphonate,[24] as well as a ribo 5'-methylene phosphonate containing thiazole-4-carboxamide as the base, has been prepared.[25] Ribo compounds having a 3'-methylene phosphonate have also been prepared.[26-28]

There are very few reports of 2'-deoxy 5'-methylene phosphonates in the literature, and these are all related to thymidine. Only the syntheses of 5'-methylene phosphonates of thymidine,[29] 3'-azidothymidine (AZT),[30,31] and 2'-deoxy-5-fluoro-uridine[32] have been reported. There have been no reports on the syntheses of 5'-methylene phosphonates derived from 2'-deoxyadenosine, 2'-deoxycytidine, or 2'-deoxyguanosine. There also have been no reports on the synthesis of 5' methylene phosphonate nucleosides having 5-iodouracil, 2-aminopurine or 2,6-diaminopurine as the base. The 5-iodouridine 5' methylene phosphonate compound would be made in an analogous manner to that used to synthesize the 5' methylene phosphonate derived from thymidine as described for compounds 33 and 37 below. The 2-aminopurine and 2,6-diaminopurine nucleoside 5' methylene phosphonates would be made in an analogous manner to that used to synthesize the 5' methylene phosphonate derived from deoxyadenosine as described for compounds 36 and 40 below.

Several ribo 5'-methylene phosphonate dimers have been synthesized. These include $UpCH_2U$ and $UpCH_2A$.[33,34] Several ribo 3'-methylene phosphonate dimers,[33] as well as a trimer[28] have been synthesized. These ribo dimers and trimer were prepared using the diester method of oligonucleotide synthesis.[35,36] This method suffers from low product yields, and difficulties in purification of the final product.[35,36] The method is generally not useful in the preparation of longer oligonucleotides. Recently, a ribo oligonucleotide 10-mer consisting of 5'-methylene phosphonates, $ApA(pCH_2A)_8$, was prepared enzymatically using polynucleotide phosphorylase.[37] This technique, however, cannot be used for the preparation of oligonucleotides having a defined sequence of mixed bases.

Only one 2'-deoxy dimer, $TpCH_2T$, and one 2'-deoxy trimer, $TpCH_2TpCH_2T$, have been reported in the literature.[29] Only the 5'-methylene phosphonate derived from thymidine was used in the dimer and trimer. No mixed base 2'-deoxy 5'-methylene phosphonate dimers or longer mixed base, 2'-deoxy 5'-methylene phosphonate oligonucleotides have been reported. Additionally, no 2'-deoxy 5'-methylene phosphonate oligonucleotides longer than a 3-mer of any kind have been reported. However, recently the synthesis of oligodeoxynucleotides containing 5'-methylene phosphonates of 2'-deoxy-4'-carbocyclic nucleosides has been reported W. Frick and S. W. Schneller, Meetings Abstract, Conference on Nucleic Acid Therapeutics, Jan. 13–17, 1991, Clearwater Beach, Fla., p63).

The present invention relates to the synthesis of 2'-deoxy-5'-methylene phosphonate oligonucleotides of length 2–30 of mixed base composition. These oligodeoxynucleotides are prepared using the phosphotriester method[38] from suitably protected 2'-deoxy 5'-methylene phosphonate nucleotide monomers. We prepared novel 5'-methylene phosphonates in both a protected form that was suitable for oligonucleotide synthesis, as well as in a completely deprotected form. Some of the novel 5'-methylene phosphonates that were prepared were derived from 2'-deoxyadenosine, 2'-deoxycytidine, and 2'-deoxyguanosine. The monomers described herein are suitable for solid phase oligonucleotide synthesis by triester chemistry. Previous methods utilized diester chemistry which is more difficult and generates low yields of product. Oligonucleotides containing 2'-deoxy-2'-fluoro-ribonucleotides are of interest because the conformation of the sugar closely resembles that of RNA and consequently these oligonucleotides have a higher affinity to DNA than normal oligodeoxyribonucleotides (M. Ikehara, Heterocycles 1984, 21, 75).

DISCLOSURE OF THE INVENTION

The present invention discloses oligonucleotides and methods for their synthesis of formula (I):

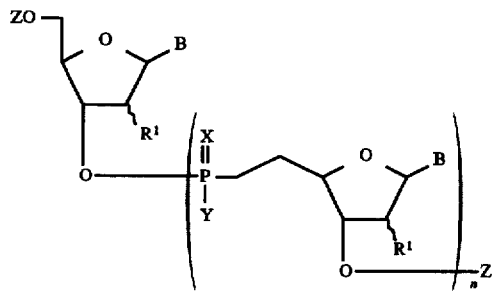

and stereoisomers thereof, wherein each B is independently a purine or pyrimidine base or modified form each Z is independently a noninterfering substituent, preferably hydrogen, $PO_3^-$ or a protecting group; each $R^1$ is independently hydrogen, hydroxyl, fluorine or methyl ester; each Y is independently $OR^2$, $N(R^2)_2$ or $SR^2$ wherein, each $R^2$ is independently hydrogen or alkyl (1–12 C); X is selected from oxygen and sulfur; n is an integer from 1 to 200. Bases such as adenine, guanine, cytosine, thymine and uracil as well as modified forms (base analogs) such as 5-methylcytosine, aziridinylcytosine, 8-hydroxy-$N^6$-methyladenine, pseudoisocytosine and inosine are preferred. The oligonucleotides contain one or more 5' methylene phosphonate linkages. The oligonucleotides may be synthesized from derivatives disclosed herein of monomers of formula (II):

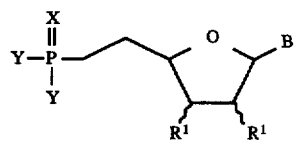

wherein B is a purine or pyrimidine base or modified form; each $R^1$ is independently hydrogen, hydroxyl, fluorine or methyl ester; each Y is independently $OR^2$, $N(R^2)_2$ or $SR^2$ wherein, each $R^2$ is independently hydrogen or alkyl (1–12 C); and X is selected from oxygen and sulfur. Bases such as guanine, adenine, cytosine, thymine, uracil, iodouracil, 8-hydroxy-$N^6$-methyladenine, aziridinylcytosine, 2-aminopurine, 2, 6-diaminopurine or other base analogs or altered forms may be utilized. Alternative monomer structures, such as 2',3' epoxides and 2',3'dideoxy didehydro sugars may also be synthesized.

The free 5'-methylene phosphonate nucleosides present enzymatically nonhydrolysable isosteres of mononucleotides. As such they can be converted intracellularly by cellular kinases to the corresponding nucleoside phosphono triphosphates, incorporated into DNA by polymerases and thus interfere with cellular metabolism. Thus, such nucleoside phosphonates potentially exhibit antiviral and antitumour activity. For example, several acyclic methylene phosphonates such as the methylene phosphonates derived from ganciclovir, and acyclovir are potent antivirals.[39-42] Other nucleoside phosphonates have been claimed in a patent application (Elmer Reist et al, Stanford Research Institute, PCT publication no. WO 84/04748). The novel 5'-methylene compounds that are described herein thus have useful antiviral or antitumour activities.

The oligonucleotide and nucleoside monomer compounds possess antiviral activity and can be used in the control or prevention of viral infections, e.g. of herpes simplex vital infections. The in vitro activity of the compounds of formula I and their tautomers in inhibiting herpes simplex virus type 2 (HSV-2) can be demonstrated by means of the following plaque reduction procedure. Host VERO cells are infected with virus stock containing a known number of infectious virions in the presence of various concentrations of compound. Plaques in the cell monolayer are then counted and compared to untreated controls and to acydovir treated controls. The degree of inhibition at each concentration of compound is expressed as a percentage of the control titer (100%). The $IC_{50}$ value, namely the concentration of compound which inhibits viral activity by 50%, is then calculated. The results that are obtained with representative compounds show that virus titer reductions occur.

The compounds disclosed herein can be used as medicaments in the form of pharmaceutical preparations which contain them in association with a compatible pharmaceutical carrier material. This can be an organic or inorganic carrier suitable for enteral, e.g. oral, or parenteral administration. Examples of such carriers are water, gelatin, gum arabic, lactose, starch, magnesium stearate, talc, vegetable oils, polyalkylene glycols and petroleum jelly. The pharmaceutical preparations can be made up in a solid form, e.g. as tablets, dragees, suppositories or capsules, or in a liquid form, e.g. as solutions, suspensions or emulsions; they may be subjected to standard pharmaceutical operations, e.g. sterilization and/or may contain adjuvants, e.g. preserving, stabilizing, wetting or emulsifying agents, salts for varying the osmotic pressure or buffers. The compounds may also be formulated in a manner suitable for administration as an aerosol. They may also contain other therapeutically valuable substances.

The compounds disclosed herein and their tautomers can be administered for the control or prevention of viral infection, such as herpes simplex viral infections, to warm-blooded animals in need of such treatment. The disclosed compounds and their tautomers can be administered to adult humans in a daily dosage of from about 1 to 1000 mg, preferably about 5 to 500 mg. The daily dosage may be administered as a single dose or in divided doses. The above dosage range is given by way of example only and can be varied upwards or downwards depending on factors such as the particular compound being administered, the route of administration, the severity of the indication being treated and the condition of the patient.

Experimental Section

General. Flash chromatography refers to the procedure of Still et. al.[43] Drying refers to drying over $Na_2SO_4$, filtration, and concentration. All reactions requiring dry solvents were run under a dry argon atmosphere.

The following six tables show structures for compounds 1 through 90.

TABLE 1

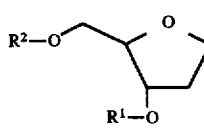

| Compound | B | $R^1$ | $R^2$ |
|---|---|---|---|
| 1 | $G^{Ib}$ | H | H |
| 3 | $C^{Bz}$ | H | H |
| 5 | $A^{Bz}$ | H | H |
| 2 | $G^{Ib}$ | H | DMT |
| 4 | $C^{Bz}$ | H | DMT |
| 6 | $A^{Bz}$ | H | DMT |
| 7 | T | H | DMT |
| 8 | $G^{Ib}$ | TBS | H |
| 9 | $C^{Bz}$ | TBS | H |
| 10 | $A^{Bz}$ | TBS | H |
| 11 | T | TBS | H |
| 12 | $T^{Bn}$ | Bn | H |

For tables 1–6; G = guanine; C = cytosine; A = adenine; T = thymine; $G^{Ib}$ = $N^2$-isobutyrylguanine; $C^{Bz}$ = $N^4$-benzoylcytosine; $A^{Bz}$ = $N^6$-benzoyladenine; $T^{Bn}$ = $N^3$-benzylthymine; Bn = benzyl; DMT = 4,4'-dimethoxytrityl; TBS = t-butyldimethylsilyl; +HTEA = hydrogentriethylammonium

TABLE 2

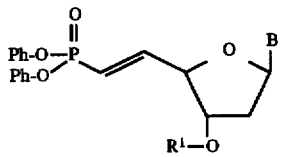

| Compound | B | $R^1$ |
|---|---|---|
| 13 | $G^{Ib}$ | TBS |
| 15 | $C^{Bz}$ | TBS |
| 17 | $A^{Bz}$ | TBS |
| 19 | T | TBS |
| 21 | $T^{Bn}$ | Bn |

For definition of abbreviations, see Table 1.

TABLE 3

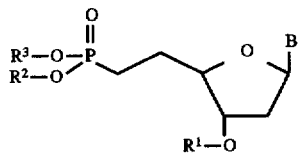

| Compound | B | $R^1$ | $R^2$ | $R^3$ |
|---|---|---|---|---|
| 14 | $G^{Ib}$ | TBS | Ph | Ph |
| 16 | $C^{Bz}$ | TBS | Ph | Ph |
| 18 | $A^{Bz}$ | TBS | Ph | Ph |
| 20 | T | TBS | Ph | Ph |
| 22 | $T^{Bn}$ | Bn | Ph | Ph |
| 23 | $T^{Bn}$ | Bn | Me | Me |
| 24 | $T^{Bn}$ | H | Me | Me |
| 25 | $T^{Bn}$ | Bn | Bn | Bn |
| 26 | $G^{Ib}$ | H | Ph | Ph |
| 27 | $C^{Bz}$ | H | Ph | Ph |
| 28 | $A^{Bz}$ | H | Ph | Ph |
| 29 | T | H | Ph | Ph |
| 30 | $G^{Ib}$ | H | Me | Me |
| 31 | $C^{Bz}$ | H | Me | Me |
| 32 | $A^{Bz}$ | H | Me | Me |
| 33 | T | H | Me | Me |
| 34 | $G^{Ib}$ | H | H | H |
| 35 | $C^{Bz}$ | H | H | H |
| 36 | $A^{Bz}$ | H | H | H |
| 37 | T | H | H | H |
| 38 | G | H | H | H |
| 39 | C | H | H | H |
| 40 | A | H | H | H |
| 41 | $G^{Ib}$ | DMT | Ph | Ph |
| 42 | $C^{Bz}$ | DMT | Ph | Ph |
| 43 | $A^{Bz}$ | DMT | Ph | Ph |
| 44 | T | DMT | Ph | Ph |
| 45 | $G^{Ib}$ | DMT | Ph | +HTEA |
| 46 | $C^{Bz}$ | DMT | Ph | +HTEA |
| 47 | $A^{Bz}$ | DMT | Ph | +HTEA |
| 48 | T | DMT | Ph | +HTEA |

For definition of abbreviations, see Table 1.

TABLE 4

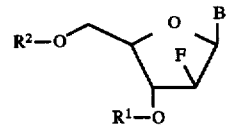

| Compound | B | $R^1$ | $R^2$ |
|---|---|---|---|
| 49 | $G^{Ib}$ | H | H |
| 51 | $C^{Bz}$ | H | H |
| 53 | $A^{Bz}$ | H | H |
| 50 | $G^{Ib}$ | H | DMT |
| 52 | $C^{Bz}$ | H | DMT |
| 54 | $A^{Bz}$ | H | DMT |
| 55 | T | H | DMT |
| 56 | $G^{Ib}$ | TBS | H |
| 57 | $C^{Bz}$ | TBS | H |
| 58 | $A^{Bz}$ | TBS | H |
| 59 | T | TBS | H |

For definition of abbreviations, see Table 1.

TABLE 5

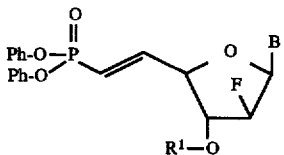

| Compound | B | R¹ |
| --- | --- | --- |
| 60 | $G^{Ib}$ | TBS |
| 62 | $C^{Bz}$ | TBS |
| 64 | $A^{Bz}$ | TBS |
| 66 | T | TBS |

For definition of abbreviations, see Table 1.

TABLE 6

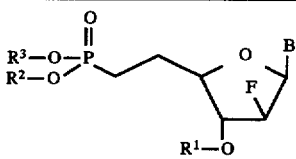

| Compound | B | R¹ | R² | R³ |
| --- | --- | --- | --- | --- |
| 61 | $G^{Ib}$ | TBS | Ph | Ph |
| 63 | $C^{Bz}$ | TBS | Ph | Ph |
| 65 | $A^{Bz}$ | TBS | Ph | Ph |
| 67 | T | TBS | Ph | Ph |
| 68 | $G^{Ib}$ | H | Ph | Ph |
| 69 | $C^{Bz}$ | H | Ph | Ph |
| 70 | $A^{Bz}$ | H | Ph | Ph |
| 71 | T | H | Ph | Ph |
| 72 | $G^{Ib}$ | H | Me | Me |
| 73 | $C^{Bz}$ | H | Me | Me |
| 74 | $A^{Bz}$ | H | Me | Me |
| 75 | T | H | Me | Me |
| 76 | $G^{Ib}$ | H | H | H |
| 77 | $C^{Bz}$ | H | H | H |
| 78 | $A^{Bz}$ | H | H | H |
| 79 | T | H | H | H |
| 80 | G | H | H | H |
| 81 | C | H | H | H |
| 82 | A | H | H | H |
| 83 | $G^{Ib}$ | DMT | Ph | Ph |
| 84 | $C^{Bz}$ | DMT | Ph | Ph |
| 85 | $A^{Bz}$ | DMT | Ph | Ph |
| 86 | T | DMT | Ph | Ph |
| 87 | $G^{Ib}$ | DMT | Ph | +HTEA |
| 88 | $C^{Bz}$ | DMT | Ph | +HTEA |
| 89 | $A^{Bz}$ | DMT | Ph | +HTEA |
| 90 | T | DMT | Ph | +HTEA |

For definition of abbreviations, see Table 1.

$N^2$-Isobutyryl-2'-deoxyguanosine (1)

The acylation by transient protection method of R. A. Jones[44] was used. To a stirred mixture of 4.28 g (15.0 mmol) of 2'-deoxyguanosine monohydrate (that was first concentrated from dry pyridine) in 150 mL of dry pyridine that was cooled on an ice water bath was added 9.75 mL (76.8 mmol, 5.12 equiv) of chlorotrimethylsilane dropwise, over several minutes. After 30 min., 12.8 mL (76.9 mmol, 5.13 equiv.) of isobutyric anhydride was added dropwise, over several minutes. The ice bath was removed and stirring was continued for 2 h. The reaction mixture was then cooled on an ice water bath, and 30 mL of cold $H_2O$ was added to the reaction. After 15 min., 30 mL of concentrated aqueous ammonia was added. The reaction was stirred for 30 min., and then concentrated. The residue was taken up in 100 mL of $H_2O$ and extracted with $Et_2O$. The title compound was either crystallized from the aqueous layer, or was isolated by flash column chromatography.

$N^2$-Isobutyryl-5'-O-(4,4'-dimethoxytrityl)-2'-deoxyguanosine (2)

The tritylation procedure of Jones[45] was modified such that no DMAP was used. To 3.37 g (10.0 mmol) of $N^2$-isobutyryl-2'-deoxyguanosine (that was first concentrated from dry pyridine) in 50 mL of dry pyridine, was added 4.06 g (12.0 mmol, 1.20 equiv.) of 4,4'-dimethoxytrityl chloride. The reaction was stirred for 15 h, and then concentrated. The residue was partitioned between $CH_2Cl_2$ and 0.5% aq. $NaHCO_3$, shaken, and separated. The organic layer was washed with 0.5% aq. $NaHCO_3$ and dried. The crude product was purified by flash chromatography.

$N^4$-Benzoyl-2'-deoxycytidine (3)

This compound was prepared from 2'-deoxycytidine monohydrate by the same procedure used for the preparation of $N^2$-isobutyryl-2'-deoxyguanosine except that 9.0 mL (77.5 mmol, 5.17 equiv.) of benzoyl chloride was used instead of isobutyric anhydride.

$N^4$-Benzoyl-5'-O-(4,4'-dimethoxytrityl)-2'-deoxycytidine (4)

This compound was prepared from $N^4$-benzoyl-2'-deoxycytidine by the same procedure used for the preparation of $N^2$-isobutyryl-5'-O-(4,4'-dimethoxytrityl)-2'-deoxyguanosine.

$N^6$-Benzoyl-2'-deoxyadenosine (5)

This compound was prepared from 2'-deoxyadenosine monohydrate by the same procedure used for the preparation of $N^4$-benzoyl-2'-deoxycytidine.

$N^6$-Benzoyl-5'-O-(4,4'-dimethoxytrityl)-2'-deoxyadenosine (6)

This compound was prepared from $N^6$-benzoyl-2'-deoxyadenosine by the same procedure used for the preparation of $N^2$-isobutyryl-5'-O-(4,4'-dimethoxytrityl)-2'-deoxyguanosine.

5'-O-(4,4'-Dimethoxytrityl)-thymidine (7)

This compound was prepared from thymidine by the same procedure used for the preparation of $N^2$-isobutyryl-5'-O-(4,4'-dimethoxytrityl)-2'-deoxyguanosine.

3'-O-t-Butyldimethylsilyl-$N^2$-isobutyryl-2'-deoxyguanosine (8)

To a stirred solution of 2.00 g (3.13 mmol) of $N^2$-isobutyryl-5'-O-(4,4'-dimethoxytrityl)-2'-deoxyguanosine and 1.54 g (22.6 mmol, 7.22 equiv.) of imidazole in 12.5 mL of dry DMF was added 1.16 g (7.70 mmol, 2.46 equiv.) of t-butyldimethylsilyl chloride. The reaction was stirred at room temperature for 3.5 h and then concentrated. The residue was partitioned between $CH_2Cl_2$ and $H_2O$, shaken, and separated. The organics were washed with $H_2O$ and concentrated (not dried). The crude residue was then stirred in 100 mL of 80% aq. HOAc for 1.5 h and then concentrated. The residue was partitioned between $CH_2Cl_2$ and $H_2O$, shaken, and separated. The organics were washed with sat. aq. $NaHCO_3$, $H_2O$, and dried. The crude product was purified by flash chromatography on a 40 mm column using one column volume of 2% TEA in $CH_2Cl_2$, then one column volume of 2% TEA and 2% MeOH in $CH_2Cl_2$, and then 2% TEA and 4% MeOH in $CH_2Cl_2$. The product was concentrated from toluene affording 1.18 g (83.7% yield).

3'-O-t-Butyldimethylsilyl-$N^4$-benzoyl-2'-deoxycytidine (9)

This compound was prepared from $N^4$-benzoyl-5'-O-(4,4'-dimethoxytrityl)-2'-deoxycytidine by the same procedure used for the preparation of 3'-O-t-butyldimethylsilyl-$N^2$-isobutyryl-2'-deoxyguanosine.

3'-O-t-Butyldimethylsilyl-N$^6$-benzoyl-2'-deoxyadenosine (10)

This compound was prepared from N$^6$-benzoyl-5'-O-(4,4'-dimethoxytrityl)-2'-deoxyadenosine by the same procedure used for the preparation of 3'-O-t-butyldimethylsilyl-N$^2$-isobutyryl-2'-deoxyguanosine.

3'-O-t-Butyldimethylsilylthymidine (11)

This compound was prepared from 5'-O-(4,4'-dimethoxytrityl)-thymidine by the same procedure used for the preparation of 3'-O-t-butyldimethylsilyl-N$^2$-isobutyryl-2'-deoxyguanosine.

3'-O,N$^3$-Dibenzylthymidine (12)

To a stirred solution of 2.18 g of 5'-O-(4,4'-dimethoxytrityl)-thymidine (4.00 mmol) in 52 mL of dry DMF was carefully added 2.00 g of a 60% oil dispersion of NaH. The reaction was stirred at room temperature for 5 min. To the mixture was added 4.77 mL (40.1 mmol, 10.0 equiv.) of benzyl bromide dropwise, over several minutes. After 1 h, the reaction was cooled on an ice-water bath. Then, 12 mL of sat. aq. NaHCO$_3$ was carefully added (vigorous hydrogen gas evolution) dropwise, over several minutes. The mixture was stirred for 10 min, and then concentrated. The residue was then stirred in 100 mL of 80% aq. HOAc at room temperature for 1.5 h, and then concentrated. The crude residue was partitioned between CH$_2$Cl$_2$ and H$_2$O, shaken, and separated. The organic layer was washed with sat. aq. NaHCO$_3$, H$_2$O, and then dried. The crude product was purified by flash chromatography on a 50 mm column using two column volumes of CH$_2$Cl$_2$, two column volumes of 1% MeOH in CH$_2$Cl$_2$, and then 2.5% MeOH in CH$_2$Cl$_2$ as eluents. This afforded 1.49 g of product (88.2% yield) as a colorless solid.

Diphenyl [9-(3-O-t-Butyldimethylsilyl-2,5,6-trideoxy-β-D-ribo-hex-5-enofuranosyl)-N$^2$-isosbutyrylguanine]-6'-phosphonate (13)

Literature methods[39] were adapted for the preparation of the title compound. To a solution of 106 mg of 3'-O-t-butyldimethylsilyl-N$^2$-isobutyryl-2'-deoxyguanosine (0.236 mmol) and 294 mg of dicyclohexylcarbodiimide DCC (1.42 mmol, 6.02 equiv.) in 1.3 mL of dry DMSO was added 11.3 mg of methylphosphonic acid (0.118 mmol, 0.50 equiv.). The reaction was stirred at room temperature. After 18 h; dry pyridine (0.080 mL) and then 120 mg (0.236 mmol, 1.00 equiv.) of diphenyl [(triphenylphosphoranylidene)methyl] phosphonate[46] were added. Another 0.80 mL of dry DMSO was added. The reaction was stirred at room temperature. After 27 h, the reaction was diluted with CH$_2$Cl$_2$, washed with 2×H$_2$O, and dried. The crude material was flashed on a 25 mm column using one column volume of CH$_2$Cl$_2$, then one column volume of 3% MeOH in CH$_2$Cl$_2$, and then 6% MeOH in CH$_2$Cl$_2$ as eluents. The product containing fractions were combined and concentrated. The product was purified again purified by flash chromatography on a 25 mm column using one column volume of 12.5% EtOAc in CH$_2$Cl$_2$, then one column volume of 25% EtOAc in CH$_2$Cl$_2$, and then 50% EtOAc in CH$_2$Cl$_2$ as eluents. This procedure afforded 9.4 mg (6.0% yield) of product.

Diphenyl [9-(3-O-t-Butyldimethylsilyl-2,5,6-trideoxy-β-D-ribohexofuranosyl)-N$^2$-isobutyrylguanine]-6'-phosphonate (14)

To a solution of 9.4 mg (0.0138 mmol) of diphenyl [9-(3-O-t-butyldimethylsilyl-2,5,6-trideoxy-β-D-ribo-hex-5-enofuranosyl)-N$^2$-isosbutyrylguanine]-6'-phosphonate in 20 mL of MeOH was added a catalytic amount of 10% Pd on carbon. The mixture was hydrogenated at 260 psi of H$_2$ (in a Parr reaction vessel) for 3 h. The mixture was filtered through Celite and concentrated. The crude product was purified by flash chromatography on a 15 mm column using one column volume of CH$_2$Cl$_2$, then one column volume of 12.5% EtOAc in CH$_2$Cl$_2$, then one column volume of 25% EtOAc in CH$_2$Cl$_2$, and then 50% EtOAc in CH$_2$Cl$_2$ as eluents. This procedure afforded 2.0 mg (21.3% yield) of product.

Diphenyl [1-(3-O-t-Butyldimethylsilyl-2,5,6-trideoxy-β-D-ribo-hex-5-enofuranosyl)-N$^4$-benzoylcytosine]-6'-phosphonate (15)

This compound is prepared from 3'-O-t-butyldimethylsilyl-N$^4$-benzoyl-2'-deoxycytidine by the same procedure used for the preparation of diphenyl [9-(3-O-t-butyldimethylsilyl-2,5,6-trideoxy-β-D-ribo-hex-5-enofuranosyl)-N$^2$-isobutyrylguanosine]-6'-phosphonate.

Diphenyl [1-(3-O-t-Butyldimethylsilyl-2,5,6-trideoxy-β-D-ribohexofuranosyl)-N$^4$-benzoylcytosine]-6'-phosphonate (16)

This compound is prepared from diphenyl [1-(3-O-t-butyldimethylsilyl-2,5,6-trideoxy-β-D-ribo-hex-5-enofuranosyl)-N$^4$-benzoylcytosine]-6'-phosphonate by the same procedure used for the preparation of diphenyl [9-(3-O-t-butyldimethylsilyl-2,5,6-trideoxy-β-D-ribohexofuranosyl)-N$^2$-isobutyrylguanosine]-6'-phosphonate.

Diphenyl [9-(3-O-t-Butyldimethylsilyl-2,5,6-trideoxy-β-D-ribo-hex-5-enofuranosyl)-N$^6$-benzoyladenine]-6'-phosphonate (17)

This compound is prepared from 3'-O-t-butyldimethylsilyl-N$^6$-benzoyl-2'-deoxyadenosine by the same procedure used for the preparation of diphenyl [9-(3-O-t-butyldimethylsilyl-2,5,6-trideoxy-β-D-ribo-hex-5-enofuranosyl)-N$^2$-isobutyrylguanosine]-6'-phosphonate.

Diphenyl [9-(3-O-t-Butyldimethylsilyl-2,5,6-trideoxy-β-D-ribohexofuranosyl)-N$^6$-benzoyladenine]-6'-phosphonate (18)

This compound is prepared from diphenyl [9-(3-O-t-butyldimethylsilyl-2,5,6-trideoxy-β-D-ribo-hex-5-enofuranosyl)-N$^6$-benzoyladenine]-6'-phosphonate by the same procedure used for the preparation of diphenyl [9-(3-O-t-butyldimethylsilyl-2,5,6-trideoxy-β-D-ribohexofuranosyl)-N$^2$-isobutyrylguanosine]-6'-phosphonate.

Diphenyl [1-(3-O-t-Butyldimethylsilyl-2,5,6-trideoxy-β-D-ribo-hex-5-enofuranosyl)-thymine]-6'-phosphonate (19)

This compound is prepared from 3'-O-t-butyldimethylsilylthymidine by the same procedure used for the preparation of diphenyl [9-(3-O-t-butyldimethylsilyl-2,5,6-trideoxy-β-D-ribo-hex-5-enofuranosyl)-N$^2$-isobutyrylguanosine]-6'-phosphonate.

Diphenyl [1-(3-O-t-Butyldimethylsilyl-2,5,6-trideoxy-β-D-ribohexofuranosyl), thymine]-6'-phosphonate (20)

This compound is prepared from diphenyl [1-(3-O-t-butyldimethylsilyl-2,5,6-trideoxy-β-D-ribo-hex-5-enofuranosyl)-thymine]-6'-phosphonate by the same procedure used for the preparation of diphenyl [9-(3-O-t-butyldimethylsilyl-2,5,6-trideoxy-β-D-ribohexofuranosyl)-N$^2$-isobutyrylguanosine]-6'-phosphonate.

Diphenyl [1-(3-O-Benzyl-2,5,6-trideoxy-β-D-ribo-hex-5-enofuranosyl)-N$^3$-benzylthymine]-6'-phosphonate (21)

The title compound was prepared by modification of related known procedures.[13,19] To a stirred solution of 300 mg of 3'-O,N$^3$-dibenzylthymidine (0.710 mmol) and 874 mg of. (4.24 mmol, 5.97 equiv.) of dicyclohexylcarbodiimide (DCC), in 2.37 mL of DMSO was added 0.356 mL of a 1.0M solution (0.356 mmol, 0.50 equiv.) of orthophosphoric acid (Aldrich) in DMSO. The reaction was stirred at room temperature. After 19 h, 0.237 mL of dry pyridine was added, followed by 412 mg (0.710 mmol, 1.0 equiv.) of diphenyl [(triphenylphosphoranylidene)methyl] phosphonate. The reaction was stirred for 31 h. The reaction mixture was partitioned between $CH_2Cl_2$ and $H_2O$, shaken and separated. The organic layer was washed with $H_2O$ and dried. The residue was purified by flash chromatography on a 25 mm column using one column volume of $CH_2Cl_2$, one column volume of 5% EtOAc in $CH_2Cl_2$, and then 10% EtOAc in $CH_2Cl_2$ as eluents. This afforded 334 mg (80.5% yield) of product.

Diphenyl [1-(3-O-Benzyl-2,5,6-trideoxy-β-D-ribohexofuranosyl)-$N^3$-benzylthymine]-6'-phosphonate (22)

To a stirred solution of 334 mg (0.513 mmol) of diphenyl [1-(3-O-benzyl-2,5,6-trideoxy-β-D-ribo-hex-5-enofuranosyl)-$N^3$-benzylthymine]-6'-phosphonate in 7.7 mL of dry $Et_2O$ was added 307 mg (1.03 mmol, 2.01 equiv.) of 2,4,6-tri-isopropylbenzenesulphonyl hydrazide,[47] followed by 0.143 mL of dry TEA. The reaction was refluxed for 14 h. The mixture was partitioned between $Et_2O$ and sat. aq. $NaHCO_3$, shaken, and separated. The organic layer was washed with $H_2O$ and dried. The residue was purified by flash chromatography on a 25 mm column using one column volume of $CH_2Cl_2$, one column volume of 5% EtOAc in $CH_2Cl_2$, and then 10% EtOAc in $CH_2Cl_2$ as eluents. This afforded 244 mg (72.8% yield) of product.

Dimethyl [1-(3-O-Benzyl-2,5,6-trideoxy-β-D-ribohexofuranosyl)-$N^3$-benzylthymine]-6'-phosphonate (23)

Commercially available CsF (100 mg) was flame dried while under vacuum, and allowed to cool to room temperature. To the dried solid was added 3.00 mL of dry MeOH, followed by 143 mg (0.219 mmol) of diphenyl [1-(3-O-benzyl-2,5,6-trideoxy-β-D-ribohexofuranosyl)-$N^3$-benzylthymine]-6'-phosphonate. The reaction was stirred for 20 h, and then concentrated. The residue was partitioned between $CH_2Cl_2$ and $H_2O$, shaken, and separated. The organics were washed with $H_2O$ and dried. The residue was purified on a 25 mm column using one column volume of $CH_2Cl_2$, one column volume of 2.5% MeOH in $CH_2Cl_2$, and then 5% MeOH in $CH_2Cl_2$ as eluents. This procedure afforded 85.9 mg (74.0% yield) of product.

Dimethyl [1-(2,5,6-Trideoxy-β-D-ribohexofuranosyl)-$N^3$-benzylthymine]-6'-phosphonate (24)

Known literature methods[48] were adapted to remove the benzyl protecting group from the 3'-oxygen. Dimethyl [1-(3-O-benzyl-2,5,6-trideoxy-β-D-ribohexofuranosyl)-$N^3$-benzylthymine]-6'-phosphonate (3.0 mg, 0.00567 mmol) was added to a 4.4% solution of $HCO_2H$ in MeOH (prepared from 96% $HCO_2H$) followed by a catalytic amount of 10% Pd on carbon. The reaction was stirred at room temperature for 19 h. The reaction was then filtered through Celite and concentrated. This procedure afforded 2.0 mg (80.6% yield) of product as a colorless solid.

Dibenzyl [1-(3-O-Benzyl-2,5,6-trideoxy-β-D-ribohexofuranosyl)-$N^3$-benzylthymine]-6'-phosphonate (25)

This procedure was based on a related procedure.[25] To a solution of 416 mg (0.638 mmol) of diphenyl [1-(3-O-benzyl-2,5,6-trideoxy-β-D-ribohexofuranosyl)-$N^3$-benzylthymine]-6'-phosphonate in 3.0 mL of benzyl alcohol, was added 2.0 mL of a solution prepared by the addition of 200 mg of NaH to 16.7 mL of benzyl alcohol. After 1 h, the reaction mixture was diluted with 50 mL of $Et_2O$. Excess gaseous $CO_2$ was bubbled into the mixture. A gel like mixture formed which was dissolved in EtOAc. This solution was concentrated onto silica gel. The silica gel was loaded onto a previously equilibrated 25 mm column and eluted with one column volume of $CH_2Cl_2$, then one column volume of 10% EtOAc in $CH_2Cl_2$, and then 20% EtOAc in $CH_2Cl_2$ as eluents. This afforded 127 mg (29.3% yield) of product.

Diphenyl [9-(2,5,6-Trideoxy-β-D-ribohexofuranoxyl)-$N^2$-isobutyrylguanine]-6'-phosphonate (26)

This reaction is based on a similar procedure by Barton et al.[30] To 5.00 mmol of diphenyl [9-(3-O-t-butyldimethylsilyl-2,5,6-trideoxy-β-D-ribohexofuranosyl)-$N^2$-isobutyrylguanine]-6'-phosphonate in 100 mL of dry THF is added 5.5 mL (5.5 mmol, 1.1 equiv.) of a 1.00M solution of tetrabutylammonium fluoride (TBAF) in THF. The reaction is stirred at room temperature for 1 h. Then 20 mL of MeOH is added. The reaction is stirred for 5 min., and then concentrated. The residue is purified by flash chromatography.

Diphenyl [1-(2,5,6-Trideoxy-β-D-ribohexofuranosyl)-$N^4$-benzoylcytosine]-6'-phosphonate (27)

This compound is prepared from diphenyl [1-(3-O-t-butyldimethylsilyl-2,5,6-trideoxy-β-D-ribohexofuranosyl)-$N^4$-benzoylcytosine]-6'-phosphonate by the same procedure used for the preparation of diphenyl [9-(2,5,6-trideoxy-β-D-ribohexofuranosyl)-$N^2$-isobutyrylguanine]-6'-phosphonate.

Diphenyl [9-(2,5,6-Trideoxy-β-D-ribohexofuranosyl)-$N^6$-benzoyladenine]-6'-phosphonate (28)

This compound is prepared from diphenyl [9-(3-O-t-butyldimethylsilyl-2,5,6-trideoxy-β-D-ribohexofuranosyl)-$N^6$-benzoyladenine]-6'-phosphonate by the same procedure used for the preparation of diphenyl [9-(2,5,6-trideoxy-β-D-ribohexofuranosyl)-$N^2$-isobutyrylguanine]-6'-phosphonate.

Diphenyl [1-(2,5,6-Trideoxy-β-D-ribohexofuranosyl)-thymine]-6'-phosphonate (29)

This compound is prepared from diphenyl [1-(3-O-t-butyldimethylsilyl-2,5,6-trideoxy-β-D-ribohexofuranosyl)-thymine]-6'-phosphonate by the same procedure used for the preparation of diphenyl [9-(2,5,6-trideoxy-β-D-ribohexofuranosyl)-$N^2$-isobutyrylguanine]-6'-phosphonate.

Dimethyl [9-(2,5,6-Trideoxy-β-D-ribohexofuranosyl)-$N^2$-isobutyrylguanine]-6'-phosphonate (30)

This compound is prepared from diphenyl [9-(2,5,6-trideoxy-β-D-ribohexofuranosyl)-$N^2$-isobutyrylguanine]-6'-phosphonate and CsF in MeOH by the same procedure used for the preparation of dimethyl [1-(3-O-benzyl-2,5,6-trideoxy-β-D-ribo-hexofuranosyl)-$N^3$-benzylthymine]-6'-phosphonate. After the aqueous extraction and drying, the crude product is purified by flash chromatography.

Dimethyl [1-(2,5,6-Trideoxy-β-D-ribohexofuranosyl)-$N^4$-benzoylcytosine]-6'-phosphonate (31)

This compound is prepared from diphenyl [1-(2,5,6-trideoxy-β-D-ribohexofuranosyl)-$N^4$-benzoylcytosine]-6'-phosphonate by the same procedure used for the preparation of dimethyl [9-(2,5,6-trideoxy-β-D-ribohexofuranosyl)-$N^2$-isobutyrylguanine]-6'-phosphonate.

Dimethyl [9-(2,5,6-Trideoxy-β-D-ribohexofuranosyl)-$N^6$-benzoyladenine]-6'-phosphonate (32)

This compound is prepared from diphenyl [9-(2,5,6-trideoxy-β-D-ribohexofuranosyl)-$N^6$-benzoyladenine]-6'-phosphonate by the same procedure used for the preparation of dimethyl [9-(2,5,6-trideoxy-β-D-ribohexofuranosyl)-$N^2$-isobutyrylguanine]-6'-phosphonate.

Dimethyl [1-(2,5,6-Trideoxy-β-D-ribohexofuranosyl)-thymine]-6'-phosphonate (33)

This compound is prepared from diphenyl [1-(2,5,6-trideoxy-β-D-ribohexofuranosyl)-thymine]-6'-phosphonate by the same procedure used for the preparation of dimethyl [9-(2,5,6-trideoxy-β-D-ribohexofuranosyl)-$N^2$-isobutyrylguanine]-6'-phosphonate.

[9-(2,5,6-Trideoxy-β-D-ribohexofuranosyl)-N²-isobutyrylguanine]-6'-phosphonic acid (34)

This reaction is based on a similar procedure by Barton et al.[30] To a stirred, ice-cooled mixture of dimethyl [9-(2,5,6-trideoxy-β-D-ribohexofuranosyl)-N²-isobutyrylguanine]-6'-phosphonate in 150 mL of $CH_2Cl_2$ is added 1.98 mL (15.0 mmol, 3.0 equiv.) of bromotrimethylsilane dropwise, over several minutes. The reaction is stirred for 30 min., and then the ice bath is removed. After stirring for an additional 10 h, 20 mL of MeOH is added. The reaction is stirred for 5 min., and then concentrated. The product is used without further purification.

[1-(2,5,6-Trideoxy-β-D-ribohexofuranosyl)-N₄-benzoylcytosine]-6'-phosphonic acid (35)

This compound is prepared from dimethyl [1-(2,5,6-trideoxy-β-D-ribohexofuranosyl)-N⁴-benzoylcytosine]-6'-phosphonate by the same procedure used for the preparation of [9-(2,5,6-trideoxy-β-D-ribohexofuranosyl)-N²-isobutyrylguanine]-6'-phosphonic acid.

[9-(2,5,6-Trideoxy-β-D-ribohexofuranosyl)-N⁶-benzoyladenine]-6'-phosphonic acid (36)

This compound is prepared from dimethyl [9-(2,5,6-trideoxy-β-D-ribohexofuranosyl)-N⁶-benzoyladenine]-6'-phosphonate by the same procedure used for the preparation of [9-(2,5,6-trideoxy-β-D-ribohexofuranosyl)-N²-isobutyrylguanine]-6'-phosphonic acid.

[1-(2,5,6-Trideoxy-β-D-ribohexofuranosyl)-thymine]-6'-phosphonic acid (37)

This compound was prepared from dimethyl [1-(2,5,6-trideoxy-β-D-ribohexofuranosyl)-thymine]-6'-phosphonate by the same procedure used for the preparation of [9-(2,5,6-trideoxy-β-D-ribohexofuranosyl)-N²-isobutyrylguanine]-6'-phosphonic acid.

[9-(2,5,6-Trideoxy-β-D-ribohexofuranosyl)-guanine]-6'-phosphonic acid (38)

The entire crude [9-(2,5,6-trideoxy-β-D-ribohexofuranosyl)-N²-isobutyrylguanine]-6'-phosphonic acid, from above, is heated in 150 mL of concentrated aqueous ammonia at 55° C. for 18 h, and then concentrated.

[1-(2,5,6-Trideoxy-β-D-ribohexofuranosyl)-cytosine]-6'-phosphonic acid (39)

This compound is prepared from [1-(2,5,6-trideoxy-β-D-ribohexofuranosyl)-N⁴-benzoylcytosine]-6'-phosphonic acid by the same procedure used for the preparation of [9-(2,5,6-trideoxy-β-D-ribohexofuranosyl)-guanine]-6'-phosphonic acid.

[9-(2,5,6-Trideoxy-β-D-ribohexofuranosyl)-adenine]-6'-phosphonic acid (40)

This compound is prepared from [9-(2,5,6-trideoxy-β-D-ribohexofuranosyl)-N⁶-benzoyladenine]-6'-phosphonic acid by the same procedure used for the preparation of [9-(2,5,6-trideoxy-β-D-ribohexofuranosyl)-guanine]-6'-phosphonic acid.

Diphenyl [9-(3-O-[4,4'-Dimethoxytrityl]-2,5,6-trideoxy-β-D-ribohexofuranosyl)-N²-isobutyrylguanine]-6'-phosphonate (41)

To 5.00 mmol of diphenyl [9-(2,5,6-trideoxy-β-D-ribohexofuranosyl)-N²-isobutyrylguanine]-6'-phosphonate (that is first concentrated from dry pyridine) in 30 mL of dry pyridine, is added 2.03 g (6.0 mmol, 1.20 equiv.) of 4,4'-dimethoxytrityl chloride. The reaction is stirred for 15 h, and then concentrated. The residue is partitioned between $CH_2Cl_2$ and 0.5% aq. $NaHCO_3$, shaken, and separated. The organic layer is washed with 0.5% aq. $NaHCO_3$ and dried. The crude product is purified by flash chromatography.

Diphenyl [1-(3-O-[4,4'-Dimethoxytrityl]-2,5,6-trideoxy-β-D-ribohexofuranosyl)-N⁴-benzoylcytosine]-6'-phosphonate (42)

This compound is prepared from diphenyl [1-(2,5,6-trideoxy-β-D-ribohexofuranosyl)-N⁴-benzoylcytosine]-6'-phosphonate by the same procedure used for the preparation of diphenyl [9-(3-O-[4,4'-dimethoxytrityl]-2,5,6-trideoxy-β-D-ribohexofuranosyl)-N²-isobutyrylguanine]-6'-phosphonate.

Diphenyl [9-(3-O-[4,4'-Dimethoxytrityl]-2,5,6-trideoxy-β-D-ribohexofuranosyl)-N⁶-benzoyladenine]-6'-phosphonate (43)

This compound is prepared from diphenyl [9-(2,5,6-trideoxy-β-D-ribohexofuranosyl)-N⁶-benzoyladenine]-6'-phosphonate by the same procedure used for the preparation of diphenyl [9-(3-O-[4,4'-dimethoxytrityl]-2,5,6-trideoxy-β-D-ribohexofuranosyl)-N²-isobutyrylguanine]-6'-phosphonate.

Diphenyl [1-(3-O-[4,4'-Dimethoxytrityl]-2,5,6-trideoxy-β-D-ribohexofuranosyl)-thymine]-6'-phosphonate (44)

This compound is prepared from diphenyl [1-(2,5,6-trideoxy-β-D-ribohexofuranosyl)-thymine]-6'-phosphonate by the same procedure used for the preparation of diphenyl [9-(3-O-[4,4'-dimethoxytrityl]-2,5,6-trideoxy-β-D-ribohexofuranosyl-N²-isobutyrylguanine]-6'-phosphonate.

Monophenyl [9-(3-O-[4,4'-Dimethoxytrityl]-2,5,6-trideoxy-β-D-ribohexofuranosyl)-N²-isobutyrylguanine]-6'-phosphonate triethylammonium salt (45)

A mixture of 3.00 mmol of diphenyl [9-(3-O-[4,4'-dimethoxytrityl]-2,5,6-trideoxy-β-D-ribohexofuranosyl)-N²-isobutyrylguanine]-6'-phosphonate is stirred in 100 mL of concentrated aqueous ammonia at room temperature. The reaction is monitored by TLC. After ca. 1 h, the mixture is concentrated. The product is purified by flash chromatography.

Monophenyl [1-(3-O-[4,4'-Dimethoxytrityl]-2,5,6-trideoxy-β-D-ribohexofuranosyl)-N⁴-benzoylcytosine]-6'-phosphonate triethylammonium salt (46)

This compound is prepared from diphenyl [1-(3-O-[4,4'-dimethoxytrityl]-2,5,6-trideoxy-β-D-ribohexofuranosyl)-N⁴-benzoylcytosine]-6'-phosphonate by the same procedure used for the preparation of monophenyl [9-(3-O-[4,4'-dimethoxytrityl]-2,5,6-trideoxy-β-D-ribohexofuranosyl)-N²-isobutyrylguanine]-6'-phosphonate triethylammonium salt.

Monophenyl [9-(3-O-[4,4'-Dimethoxytrityl]-2,5,6-trideoxy-β-D-ribohexofuranosyl)-N⁶-benzoyladenine]-6'-phosphonate triethylammonium salt (47)

This compound is prepared from diphenyl [9-(3-O-[4,4'-dimethoxytrityl]-2,5,6-trideoxy-β-D-ribohexofuranosyl)-N⁶-benzoyladenine]-6'-phosphonate by the same procedure used for the preparation of monophenyl [9-(3-O-[4,4'-dimethoxytrityl]-2,5,6-trideoxy-β-D-ribohexofuranosyl)-N²-isobutyrylguanine]-6'-phosphonate triethylammonium salt.

Monophenyl [1-(3-O-[4,4'-Dimethoxytrityl]-2,5,6-trideoxy-β-D-ribohexofuranosyl)-thymine]-6'-phosphonate triethylammonium salt (48)

This compound is prepared from diphenyl [1-(3-O-[4,4'-dimethoxytrityl]-2,5,6-trideoxy-β-D-ribohexofuranosyl)-thymine]-6'-phosphonate by the same procedure used for the preparation of monophenyl [9-(3-O-[4,4'-dimethoxytrityl]-2,5,6-trideoxy-β-D-ribohexofuranosyl)-N²-isobutyrylguanine]-6'-phosphonate triethylammonium salt.

9-(2-Deoxy-2-fluoro-β-D-arabinofuranosyl)-N²-isobutyrylguanine (49)

This compound is prepared from 9-(2-deoxy-2-fluoro-β-D-arabinofuranosyl)-guanine[49] by the same procedure used for the preparation of N²-isobutyryl-2'-deoxyguanosine.

9-[2-Deoxy-5-O-(4,4'-dimethoxytrityl)-2-fluoro-β-D-arabinofuranosyl]-N²-isobutyrylguanine (50)

This compound is prepared from 9-(2-deoxy-2-fluoro-β-D-arabinofuranosyl)-N²-isobutyrylguanine by the same procedure used for the preparation of N²-isobutyryl-5'-O-(4,4'-dimethoxytrityl)-2'-deoxyguanosine.

1-(2-Deoxy-2-fluoro-β-D-arabinofuranosyl)-N⁴-benzoylcytosine (51)

This compound is prepared from 1-(2-deoxy-2-fluoro-β-D-arabinofuranosyl)cytosine[50] by the same procedure used for the preparation of N⁴-benzoyl-2'-deoxycytidine.

1-[2-Deoxy-5-O-(4,4'-dimethoxytrityl)-2-fluoro-β-D-arabinofuranosyl]-N⁴-benzoylcytosine (52)

This compound is prepared from 1-(2-deoxy-2-fluoro-β-D-arabinofuranosyl)-N⁴-benzoylcytosine by the same procedure used for the preparation of N⁴-benzoyl-5'-O-(4,4'-dimethoxytrityl)-2'-deoxycytidine.

9-(2-Deoxy-2-fluoro-β-D-arabinofuranosyl)-N⁶-benzoyladenine (53)

This compound is prepared from 9-(2-deoxy-2-fluoro-β-D-arabinofuranosyl)adenine[49] by the same procedure used for the preparation of N⁶-benzoyl-2'-deoxyadenosine.

9-[2-Deoxy-5-O-(4,4'-dimethoxytrityl)-2-fluoro-β-D-arabinofuranosyl]-N⁶-benzoyladenine (54)

This compound is prepared from 9-(2-deoxy-2-fluoro-β-D-arabinofuranosyl)-N⁶-benzoyladenine by the same procedure used for the preparation of N⁶-benzoyl-5'-O-(4,4'-dimethoxytrityl)-2'-deoxyadenosine.

1-[2-Deoxy-5-O-(4,4'-dimethoxytrityl)-2-fluoro-β-D-arabinofuranosyl]-thymine (55)

This compound is prepared from 1-(2-deoxy-2-fluoro-β-D-arabinofuranosyl)-thymine[51] by the same procedure used for the preparation of 5'-O-(4,4'-dimethoxytrityl)-thymidine.

9-(3-O-t-Butyldimethylsilyl-2-deoxy-2-fluoro-β-D-arabinofuranosyl)-N²-isobutyrylguanine (56)

This compound is prepared from 9-[2-deoxy-5-O-(4,4'-dimethoxytrityl)-2-fluoro-β-D-arabinofuranosyl]-N²-isobutyrylguanine by the same procedure used for the preparation of 3'-O-t-butyldimethylsilyl-N²-isobutyryl-2'-deoxyguanosine.

1-(3-O-t-Butyldimethylsilyl-2-deoxy-2-fluoro-β-D-arabinofuranosyl)-N⁴-benzoylcytosine (57)

This compound is prepared from 1-[2-deoxy-5-O-(4,4'-dimethoxytrityl)- 2-fluoro-β-D-arabinofuranosyl]-N⁴-benzoylcytosine by the same procedure used for the preparation of 3'-O-t-butyldimethylsilyl-N⁴-benzoyl-2'-deoxycytidine.

9-(3-O-t-Butyldimethylsilyl-2-deoxy-2-fluoro-β-D-arabinofuranosyl)-N⁶-benzoyladenine (58)

This compound is prepared from 9-[2-deoxy-5-O-(4,4'-dimethoxytrityl)-2-fluoro-β-D-arabinofuranosyl]-N⁶-benzoyladenine by the same procedure used for the preparation of 3'-O-t-butyldimethylsilyl-N⁶-benzoyl-2'-deoxyadenosine.

1-(3-O-t-Butyldimethylsilyl-2-deoxy-2-fluoro-β-D-arabinofuranosyl)-thymine (59)

This compound is prepared from 1-[2-deoxy-5-O-(4,4'-dimethoxytrityl)-2-fluoro-β-D-arabinofuranosyl]-thymine by the same procedure used for the preparation of 3'-O-t-butyldimethylsilylthymidine.

Diphenyl [9-(3-O-t-Butyldimethylsilyl-2,5,6-trideoxy-2-fluoro-β-D-arabino-hex-5-enofuranosyl)-N²-isosbutyrylguanine]-6'-phosphonate (60)

This compound is prepared from 9-(3-O-t-butyldimethylsilyl-2-deoxy-2-fluoro-β-D-arabinofuranosyl) -N²-isobutyrylguanine by the same procedure used for the preparation of diphenyl [9-(3-O-t-butyldimethylsilyl-2,5,6-trideoxy-β-D-ribo-hex-5-enofuranosyl)-N²-isosbutyrylguanosine]-6'-phosphonate.

Diphenyl [9-(3-O-t-Butyldimethylsilyl-2,5,6-trideoxy-2-fluoro-β-D-arabinohexofuranosyl)-N²-isobutyrylguanine]-6'-phosphonate (61)

This compound is prepared from diphenyl [9-(3-O-t-butyldimethylsilyl-2,5,6-trideoxy-2-fluoro-β-D-arabino-hex-5-enofuranosyl)-N²-isobutyrylguanine]-6'-phosphonate by the same procedure used for the preparation of diphenyl [9-(3-O-t-butyldimethylsilyl-2,5,6-trideoxy-β-D-ribohexofuranosyl)-N²-isobutyrylguanine]-6'-phosphonate.

Diphenyl [1-(3-O-t-Butyldimethylsilyl-2,5,6-trideoxy-2-fluoro-β-D-arabino-hex-5-enofuranosyl)-N⁴-benzoylcytosine]-6'-phosphonate (62)

This compound is prepared from 1-(3-O-t-butyldimethylsilyl-2-deoxy-2-fluoro-β-D-arabinofuranosyl) -N⁴-benzoylcytosine by the same procedure used for the preparation of diphenyl [1-(3-O-t-butyldimethylsilyl-2,5,6-trideoxy-β-D-ribo-hex-5-enofuranosyl)-N⁴-benzoylcytosine]-6'-phosphonate.

Diphenyl [1-(3-O-t-Butyldimethylsilyl-2,5,6-trideoxy-2-fluoro-β-D-arabinohexofuranosyl)-N⁴-benzoylcytosine]-6'-phosphonate (63)

This compound is prepared from diphenyl [1-(3-O-t-butyldimethylsilyl-2,5,6-trideoxy-2-fluoro-β-D-arabino-hex-5-enofuranosyl)-N⁴-benzoylcytosine]-6'-phosphonate by the same procedure used for the preparation of diphenyl [1-(3-O+butyldimethylsilyl-2,5,6-trideoxy-β-D-ribohexofuranosyl)-N⁴-benzoylcytosine]-6'-phosphonate.

Diphenyl [9-(3-O-t-Butyldimethylsilyl-2,5,6-trideoxy-2-fluoro-β-D-arabino-hex-5-enofuranosyl)-N⁶-benzoyladenine]-6'-phosphonate (64)

This compound is prepared from 9-(3-O-t-butyldimethylsilyl-2-deoxy-2-fluoro-β-D-arabinofuranosyl) -N⁶-benzoyladenine by the same procedure used for the preparation of diphenyl [9-(3-O-t-butyldimethylsilyl-2,5,6-trideoxy-β-D-ribo-hex-5-enofuranosyl)-N⁶-benzoyladenine]-6'-phosphonate.

Diphenyl [9-(3-O-t-Butyldimethylsilyl-2,5,6-trideoxy-2-fluoro-β-D-arabinohexofuranosyl)-N⁶-benzoyladenine]-6'-phosphonate (65)

This compound is prepared from diphenyl [9-(3-O-t-butyldimethylsilyl-2,5,6-trideoxy-2-fluoro-β-D-arabino-hex-5-enofuranosyl)-N⁶-benzoyladenine]-6'-phosphonate by the same procedure used for the preparation of diphenyl [9-(3-O-t-butyldimethylsilyl-2,5,6-trideoxy-β-D-ribohexofuranosyl)-N⁶-benzoyladenine]-6'-phosphonate.

Diphenyl [1-(3-O-t-Butyldimethylsilyl-2,5,6-trideoxy-2-fluoro-β-D-arabino-hex-5-enofuranosyl)-thymine]-6'-phosphonate (66)

This compound is prepared from 1-(3-O-t-butyldimethylsilyl-2-deoxy-2-fluoro-β-D-arabinofuranosyl) -thymine by the same procedure used for the preparation of diphenyl [1-(3-O-t-butyldimethylsilyl-2,5,6-trideoxy-β-D-ribo-hex-5-enofuranosyl)-thymine]-6'-phosphonate.

Diphenyl [1-(3-O-t-Butyldimethylsilyl-2,5,6-trideoxy-2-fluoro-β-D-arabinohexofuranosyl)-thymine]-6'-phosphonate (67)

This compound is prepared from diphenyl [1-(3-O-t-butyldimethylsilyl-2,5,6-trideoxy-2-fluoro-β-D-arabino-hex-5-enofuranosyl)-thymine]-6'-phosphonate by the same procedure used for the preparation of diphenyl [1-(3-O-t-butyldimethylsilyl-2,5,6-trideoxy-β-D-ribohexofuranosyl)-thymine]-6'-phosphonate.

Diphenyl [9-(2,5,6-Trideoxy-2-fluoro-β-D-arabinohexofuranosyl)-$N^2$-isobutyrylguanine]-6'-phosphonate (68)

This compound is prepared from diphenyl [9-(3-O-t-butyldimethylsilyl-2,5,6-trideoxy-2-fluoro-β-D-arabinohexofuranosyl)-$N^2$-isobutyrylguanine]-6'-phosphonate by the same procedure used for the preparation of diphenyl [9-(2,5,6-trideoxy-β-D-ribohexofuranosyl)-$N^2$-isobutyrylguanine]-6'-phosphonate.

Diphenyl [1-(2,5,6-Trideoxy-2-fluoro-β-D-arabinohexofuranosyl)-$N^4$-benzoylcytosine]-6'-phosphonate (69)

This compound is prepared from diphenyl [1-(3-O-t-butyldimethylsilyl-2,5,6-trideoxy-2-fluoro-β-D-arabinohexofuranosyl)-$N^4$-benzoylcytosine]-6'-phosphonate by the same procedure used for the preparation of diphenyl [1-(2,5,6-trideoxy-β-D-ribohexofuranosyl)-$N^4$-benzoylcytosine]-6'-phosphonate.

Diphenyl [9-(2,5,6-Trideoxy-2-fluoro-β-D-arabinohexofuranosyl)-$N^6$-benzoyladenine]-6'-phosphonate (70)

This compound is prepared from diphenyl [9-(3-O-t-butyldimethylsilyl-2,5,6-trideoxy-2-fluoro-β-D-arabinohexofuranosyl)-$N^6$-benzoyladenine]-6'-phosphonate by the same procedure used for the preparation of diphenyl [9-(2,5,6-trideoxy-β-D-ribohexofuranosyl)-$N^6$-benzoyladenine]-6'-phosphonate.

Diphenyl [1-(2,5,6-Trideoxy-2-fluoro-β-D-arabinohexofuranosyl)-thymine]-6'-phosphonate (71)

This compound is prepared from diphenyl [1-(3-O-t-butyldimethylsilyl-2,5,6-trideoxy-2-fluoro-β-D-arabinohexofuranosyl)thymine]-6'-phosphonate by the same procedure used for the preparation of diphenyl [1-(2,5,6-trideoxy-β-D-ribohexofuranosyl)-thymine]-6'-phosphonate.

Dimethyl [9-(2,5,6-Trideoxy-2-fluoro-β-D-arabinohexofuranosyl)-$N^2$-isobutyrylguanine]-6'-phosphonate (72)

This compound is prepared from diphenyl [9-(2,5,6-trideoxy-2-fluoro-β-D-arabinohexofuranosyl)-$N^2$-isobutyrylguanine]-6'-phosphonate by the same procedure used for the preparation of dimethyl [9-(2,5,6-trideoxy-β-D-ribohexofuranosyl)-$N^2$-isobutyrylguanine]-6'-phosphonate.

Dimethyl [1-(2,5,6-Trideoxy-2-fluoro-β-D-arabinohexofuranosyl)-$N^4$-benzoylcytosine]-6'-phosphonate (73)

This compound is prepared from diphenyl [1-(2,5,6-trideoxy-2-fluoro-β-D-arabinohexofuranosyl)-$N^4$-benzoylcytosine]-6'-phosphonate by the same procedure used for the preparation of dimethyl [1-(2,5,6-trideoxy-β-D-ribohexofuranosyl)-$N^4$-benzoylcytosine]-6'-phosphonate.

Dimethyl [9-(2,5,6-Trideoxy-2-fluoro-β-D-arabinohexofuranosyl)-$N^6$-benzoyladenine]-6'-phosphonate (74)

This compound is prepared from diphenyl [9-(2,5,6-trideoxy-2-fluoro-β-D-arabinohexofuranosyl)-$N^6$-benzoyladenine]-6'-phosphonate by the same procedure used for the preparation of dimethyl [9-(2,5,6-trideoxy-β-D-ribohexofuranosyl)-$N^6$-benzoyladenine]-6'-phosphonate.

Dimethyl [1-(2,5,6-Trideoxy-2-fluoro-β-D-arabinohexofuranosyl)-thymine]-6'-phosphonate (75)

This compound is prepared from diphenyl [1-(2,5,6-trideoxy-2-fluoro-β-D-arabinohexofuranosyl)-thymine]-6'-phosphonate by the same procedure used for the preparation of dimethyl [1-(2,5,6-trideoxy-β-D-ribohexofuranosyl)-thymine]-6'-phosphonate.

[9-(2,5,6-Trideoxy-2-fluoro-β-D-arabinohexofuranosyl)-$N^2$-isobutyrylguanine], 6'-phosphonic acid (76)

This compound is prepared from dimethyl [9-(2,5,6-trideoxy-2-fluoro-β-D-arabinohexofuranosyl)-$N^2$-isobutyrylguanine]-6'-phosphonate by the same procedure used for the preparation of [9-(2,5,6-trideoxy-β-D-ribohexofuranosyl)-$N^2$-isobutyrylguanine]-6'-phosphonic acid.

[1-(2,5,6-Trideoxy-2-fluoro-15 -D-arabinohexofuranosyl)-$N^4$-benzoylcytosine]-6'-phosphonic acid (77)

This compound is prepared from dimethyl [1-(2,5,6-trideoxy-2-fluoro-β-D-arabinohexofuranosyl)-$N^4$-benzoylcytosine]-6'-phosphonate by the same procedure used for the preparation of [1-(2,5,6-trideoxy-β-D-ribohexofuranosyl)-$N^4$-benzoylcytosine]-6'-phosphonic acid.

[9-(2,5,6-Trideoxy-2-fluoro-β-D-arabinohexofuranosyl)-$N^6$-benzoyladenine]-6'-phosphonic acid (78)

This compound is prepared from dimethyl [9-(2,5,6-trideoxy-2-fluoro-β-D-arabinohexofuranosyl)-$N^6$-benzoyladenine]-6'-phosphonate by the same procedure used for the preparation of [9-(2,5,6-trideoxy-β-D-ribohexofuranosyl)-$N^6$-benzoyladenine]-6'-phosphonic acid.

[1-(2,5,6-Trideoxy-2-fluoro-β-D-arabinohexofuranosyl)-thymine]-6'-phosphonic acid (79)

This compound is prepared from dimethyl [1-(2,5,6-trideoxy-2-fluoro-β-D-arabinohexofuranosyl)-thymine]-6'-phosphonate by the same procedure used for the preparation of [1-(2,5,6-trideoxy-β-D-ribohexofuranosyl)-thymine]-6'-phosphonic acid.

[9-(2,5,6-Trideoxy-2-fluoro-β-D-arabinohexofuranosyl)-guanine]-6'-phosphonic acid (80)

This compound is prepared from [9-(2,5,6-trideoxy-2-fluoro-β-D-arabinohexofuranosyl)-$N^2$-isobutyrylguanine]-6'-phosphonic acid by the same procedure used for the preparation of [9-(2,5,6-trideoxy-β-D-ribohexofuranosyl)-guanine]-6'-phosphonic acid.

[1-(2,5,6-Trideoxy-2-fluoro-β-D-arabinohexofuranosyl)-cytosine]-6'-phosphonic acid (81)

This compound is prepared from [1-(2,5,6-trideoxy-2-fluoro-β-D-arabinohexofuranosyl)-$N^4$-benzoylcytosine]-6'-phosphonic acid by the same procedure used for the preparation of [1-(2,5,6-trideoxy-β-D-ribohexofuranosyl)-cytosine]-6'-phosphonic acid.

[9-(2,5,6-Trideoxy-2-fluoro-β-D-arabinohexofuranosyl)-adenine]-6'-phosphonic acid (82)

This compound is prepared from [9-(2,5,6-trideoxy-2-fluoro-β-D-arabinohexofuranosyl)-$N^6$-benzoyladenine]-6'-phosphonic acid by the same procedure used for the preparation of [9-(2,5,6-trideoxy-β-D-ribohexofuranosyl)-adenine]-6'-phosphonic acid.

Diphenyl [9-(3-O-[4,4'-Dimethoxytrityl]-2,5,6-trideoxy-2-fluoro-β-D-arabinohexofuranosyl)-$N^2$-isobutyrylguanine]-6'-phosphonate (83)

This compound is prepared from diphenyl [9-(2,5,6-trideoxy-2-fluoro-β-D-arabinohexofuranosyl)-$N^2$-isobutyrylguanine]-6'-phosphonate by the same procedure used for the preparation of diphenyl [9-(3-O-[4,4'-dimethoxytrityl]-2,5,6-trideoxy-β-D-ribohexofuranosyl)-$N^2$-isobutyrylguanine]-6'-phosphonate.

Diphenyl [1-(3-O-[4,4'-Dimethoxytrityl]-2,5,6-trideoxy-2-fluoro-β-D-arabinohexofuranosyl)-$N^4$-benzoylcytosine]-6'-phosphonate (84)

This compound is prepared from diphenyl [1-(2,5,6-trideoxy-2-fluoro-β-D-arabinohexofuranosyl)-$N^4$-benzoylcytosine]-6'-phosphonate by the same procedure used for the preparation of diphenyl [1-(3-O-[4,4'-dimethoxytrityl]-2,5,6-trideoxy-β-D-ribohexofuranosyl)-N⁴-benzoylcytosine]-6'-phosphonate.

Diphenyl [9-(3-O-[4,4'-Dimethoxytrityl]-2,5,6-trideoxy-2-fluoro-β-D-arabinohexofuranosyl)-N⁶-benzoyladenine]-6'-phosphonate (85)

This compound is prepared from diphenyl [9-(2,5,6-trideoxy-2-fluoro-β-D-arabinohexofuranosyl)-N⁶-benzoyladenine]-6'-phosphonate by the same procedure used for the preparation of diphenyl [9-(3-O-[4,4'-dimethoxytrityl]-2,5,6-trideoxy-β-D-ribohexofuranosyl)-N⁶-benzoyladenine]-6'-phosphonate.

Diphenyl [1-(3-O-[4,4'-Dimethoxytrityl]-2,5,6-trideoxy-2-fluoro-β-D-arabinohexofuranosyl)-thymine]-6'-phosphonate (86)

This compound is prepared from diphenyl [1-(2,5,6-trideoxy-2-fluoro-β-D-arabinohexofuranosyl)-thymine]-6'-phosphonate by the same procedure used for the preparation of diphenyl [1-(3-O-[4,4'-dimethoxytrityl]-2,5,6-trideoxy-β-D-ribohexofuranosyl)-thymine]-6'-phosphonate.

Monophenyl [9-(3-O-[4,4'-Dimethoxytrityl]-2,5,6-trideoxy-2-fluoro-β-D-arabinohexofuranosyl)-N²-isobutyrylguanine]-6'-phosphonate triethylammonium salt (87)

This compound is prepared from diphenyl [9-(3-O-[4,4'-dimethoxytrityl]-2,5,6-trideoxy-2-fluoro-β-D-arabinohexofuranosyl)-N²-isobutyrylguanine]-6'-phosphonate by the same procedure used for the preparation of monophenyl [9-(3-O-[4,4'-dimethoxytrityl]-2,5,6-trideoxy-β-D-ribohexofuranosyl)-N²-isobutyrylguanine]-6'-phosphonate triethylammonium salt.

Monophenyl [1-(3-O-[4,4'-Dimethoxytrityl]-2,5,6-trideoxy-2-fluoro-β-D-arabinohexofuranosyl)-N⁴-benzoylcytosine]-6'-phosphonate triethylammonium salt (88)

This compound is prepared from diphenyl [1-(3-O-[4,4'-dimethoxytrityl]-2,5,6-trideoxy-2-fluoro-β-D-arabinohexofuranosyl)-N⁴-benzoylcytosine]-6'-phosphonate by the same procedure used for the preparation of monophenyl [1-(3-O-[4,4'-dimethoxytrityl]-2,5,6-trideoxy-β-D-ribohexofuranosyl)-N⁴-benzoylcytosine]-6'-phosphonate triethylammonium salt.

Monophenyl [9-(3-O-[4,4'-Dimethoxytrityl]-2,5,6-trideoxy-2-fluoro-β-D-arabinohexofuranosyl)-N⁶-benzoyladenine]-6'-phosphonate triethylammonium salt (89)

This compound is prepared from diphenyl [9-(3-O-[4,4'-dimethoxytrityl]-2,5,6-trideoxy-2-fluoro-β-D-arabinohexofuranosyl)-N⁶-benzoyladenine]-6'-phosphonate by the same procedure used for the preparation of monophenyl [9-(3-O-[4,4'-dimethoxytrityl]-2,5,6-trideoxy-β-D-ribohexofuranosyl)-N⁶-benzoyladenine]-6'-phosphonate triethylammonium salt.

Monophenyl [1-(3-O-[4,4'-Dimethoxytrityl]-2,5,6-trideoxy-2-fluoro-β-D-arabinohexofuranosyl)-thymine]-6'-phosphonate triethylammonium salt (90)

This compound is prepared from diphenyl [1-(3-O-[4,4'-dimethoxytrityl]-2,5,6-trideoxy-2-fluoro-β-D-arabinohexofuranosyl)-thymine]-6'-phosphonate by the same procedure used for the preparation of monophenyl [1-(3-O-[4,4'-dimethoxytrityl]-2,5,6-trideoxy-β-D-ribohexofuranosyl)-thymine]-6'-phosphonate triethylammonium salt.

Synthesis of Oligonucleotides

Oligonucleotides are synthesized from the 5'-end to the 3'-end. The phosphotriester method of oligonucleotide synthesis described by Sproat and Gait is used.[38] Appropriately protected 3'-O-(4,4'-dimethoxytrityl)-nucleosides having a free 5'-hydroxyl group are required for the solid phase synthesis.[52] These nucleosides are affixed to a long chain alkylamine controlled pore glass (LCAA/CPG) via a succinate linker using standard methods.[38] The 3'-O-DMT group on the support bound nucleoside is cleaved with 3% (v/v) dichloroacetic acid in 1,2-dichloroethane (DCE). After washing with DCE, and then pyridine, coupling of the appropriate monophenyl nucleoside-6'-phosphonate as its triethylammonium salt is effected with the coupling agent 1-mesitylenesulphonyl-3-nitro-1,2,4-triazole (MSNT) and 1-methylimidazole (NMI) in pyridine. This coupling is allowed to occur from 15–45 minutes. The support is then washed with pyridine. The oligo containing support is then treated with an Ac₂O/lutidine/DMAP is capping solution. The capping agent and its use is described by Atkinson and Smith.[53] After capping, the support is washed with first DCE, pyridine, and then DCE again. Then the cycle is repeated (ie. deprotection, coupling, capping). After the last coupling step, the fully protected oligonucleotide is cleaved from the support and fully deprotected using a mixture of pyridine-2-carbaldoxime and tetramethylguanidine in dioxane/water.[38] This deprotection is allowed to occur at 37° C. for 20 h. After drying in vacuo, the oligonucleotide is purified by either HPLC or polyacrylamide gel electrophoresis (PAGE).

References

1. Stein, C. A.; and Cohen, J. S. *Cancer Res.*, 1988, 48, 2659–2688.
2. van der Krol, A. R.; Mol, J. N. M.; and Stuitje, A. R. *BioTechniques*, 1988, 6, 958–976.
3. Weintraub, H. M. *Scientific American*, January, 1990, 40–46.
4. J. Goodchild in "Oligodeosynucleotides: Antisense Inhibitors of Gene Expression," chapter 3, J. S. Cohen (ed.), 1989, CRC Press, Inc. Boca Raton, Fla.
5. P. B. Dervan in "Oligodeosynucleotides: Antisense Inhibitors of Gene Expression," chapter 9, J. S. Cohen (ed.), 1989, CRC Press, Inc. Boca Raton, Fla.
6. P. B. Dervan in "Nucleic Adds and Molicular ABiology," volume 2, pp 49–64, f. Eckstein and D. M. J. Lilley (eds.), 1988, Springer-Verlag, Berlin.
7. Zon, G. *Pharmaceutical Res.*, 1988, 5, 539–549.
8. C. A. Stein and J. S. Cohen in "Oligodeosynucleotides: Antisense Inhibitors of Gene Expression," chapter 5, J. S. Cohen (ed.), 1989, CRC Press, Inc. Boca Raton, Fla.
9. M. H. Caruthers in "Oligodeosynucleotides: Antisense Inhibitors of Gene Expression," chapter 1, J. S. Cohen (ed.), 1989, CRC Press, Inc. Boca Raton, Fla.
10. a. Grandas, A.; Marshall, W. S.; Nielsen, J.; and Caruthers, M. H. *Tetrahedron Lett.*, 1989, 30, 543–546. b. Brill, W. K. -D.; Tang, J. -Y.; Ma, Y. -X.; and Caruthers, M. H. *J. Amer. Chem. Soc.*; 1989, 111, 2321–2322. c. Caruthers, M. H.; Beaton, G.; Brill, W. K. -D.; Cummins, L.; Ma, Y. -X.; Marshall, W. S.; Nielsen, J.; Sasmor, H.; and Yau, E. "Synthesis and Biological Studies with Dithioate DNA." Presented at the 9th International Round Table: Nucleosides, Nucleotides, and their Biological Applications; Jul. 30–Aug. 3, 1990, Uppsala, Sweden.
11. P. S. Miller in "Oligodeosynucleotides: Antisense Inhibitors of Gene Expression," chapter 4, J. S. Cohen (ed.), 1989, CRC Press, Inc. Boca Raton, Fla.
12. Engel, R. *Chem. Rev.*, 1977, 77, 349–367.
13. Jones, G. H.; and Moffatt, J. G. *J. Amer. Chem. Soc.*, 1968, 90, 5337–5338.
14. Padyukova, N. S.; Karpeisky, M. Y.; Kolobushkina, L. I.; and Mikhailov, S. N. *Tetrahedron Lett.*, 1987, 28, 3623–3626.
15. Mikhailov, S. N.; Padyukova, N. S.; Karpeiskii, M. Y.; Kolobushkina, L. L; and Beigelman, L. N. *Collect. Czech. Chem. Commun.*, 1989, 54, 1055–1067.

16. Martin, J. C.; and Verheyden, J. P. H. *Nucleosides and Nucleotides*, 1988, 7, 365–374.
17. Hampton, A.; Perini, F.; and Harper, P. J. *Biochemistry*, 1973, 12, 1730–1736.
18. Hampton, A.; Sasaki, T.; and Paul, B. *J. Amer. Chem. Soc.*, 1973, 95, 4404–4414.
19. Montgomery, J. A.; Laseter, A. G.; and Hewson, K. *J. Het. Chem.*, 1974, 11, 211–218.
20. Hampton, A.; Sasaki, T.; Perini, F.; Slotin, L. A.; and Kappler, F. *J. Med. Chem.*, 1976, 19, 1029–1033.
21. Hampton, A.; Slotin, L. A.; Kappler, F.; Sasaki, T.; and Perini, F. *J. Med. Chem.*, 1976, 19, 1371–1377.
22. Kappler, F.; Hal, T. T.; and Hampton, A. *J. Med. Chem.*, 1986, 29, 318–322.
23. Kappler, F.; Hal, T. T.; Cotter, R. J.; Hyver, K. J.; and Hampton, A. *J. Med. Chem.*, 1986, 29, 1030–1038.
24. Fuertes, M.; Witkowski, J. T.; Streeter, D. G.; and Robins, R. K. *J. Med. Chem.*, 1974, 17, 642–645.
25. Marquez, V. E.; Tseng, C. K. H.; Gebeyehu, G.; Cooney, D. A.; Ahluwalia, G. S.; Kelley, J. A.; Dalal, M.; Fuller, R. W.; Wilson, Y. A.; and Johns, D. G. *J. Med. Chem.*, 1986, 29, 1726–1731.
26. Albrecht, J. P.; Jones, G. H.; and Moffatt, J. G. *Tetrahedron*, 1984, 40, 79–85.
27. Albrecht, H. P.; Jones, G. H.; and Moffatt, J. *Amer. Chem. Soc.*, 1970, 92, 5511–5513.
28. Mazur, A.; Tropp, B. E.; and Engel, R. *Tetrahedron*, 1984, 40, 3949–3956.
29. Cozzone, R. J.; and Kaptein, R. *FEBS Lett.*, 1983, 155, 55–60.
30. Barton, D. H. R.; Gero, S. D.; Quicklet-Sire, B.; and Samadi, M. *Tetrahedron Lett.*, 1989, 30, 4969–4972.
31. Tanaka, H.; Fukui, M.; Haraguchi, K.; Masaki, M.; and Miyasaka, T. *Tetrahedron Lett.*, 1989, 30, 2567–2570.
32. Montgomery, J. A.; Thomas, H. J.; Kisliuk, R. L.; and Gaumont, Y. *J. Med. Chem.*, 1979, 22, 109–111.
33. Jones, G. H.; Albrecht, H. P.; Damodaran, N. P.; and Moffatt, J. G. *J. Amer. Chem. Soc.*, 1970, 92, 5510–5511.
34. Griffin, J. H.; Schechter, A. N.; and Cohen, J. S. *Annals New York Academy of Sciences*, 1973, 222, 693–708.
35. B. E. Kaplan and K. Itakura in {"Synthesis and Applications of DNA and RNA," chapter 2, S. A. Narang (ed.), 1987, Academic Press, Orlando, Florida.
36. a. Crockett, G. C. *Aldrichimica Acta*, 1983, 16, 47–55. b. Agarwal, K. L.; Yamazaki, A.; Cashion, P. J.; and Khorana, H. G. *Angew. Chem. Int. Ed. Eng.*, 1972, 11, 451–459.
37. Breaker, R. R.; Gough, G. R.; and Gilham, P. T. *Nucleic Acids Res.*, 1990, 18, 3085–3086.
38. B. S. Sproat and M. J. Gait in "Oligonucleotide Synthesis: A Practical Approach," chapter 4, M. J. Gait (ed.), 1984, IRL Press, Oxford.
39. Prisbe, E. J.; Martin, J. C.; McGee, D. P. C.; Barker, M. F.; Smee, D. F.; Duke, A. E.; Matthews, T. R.; and Verheyden, J. P. H. *J. Med. Chem.*, 1986, 29, 671–675.
40. Duke, A. E.; Smee, D. F.; Chernow, M.; Boehme, R.; and Matthews, T. R. *Antiviral Research*, 1986, 6, 299–308.
41. Reist, E. J.; Sturm, P. A.; Pong, R. Y.; and Sidwess, R. W. *Nucleosides and Nucleotides*, 1989, 8, 919–922.
42. Sidwell, R. w.; Huffman, J. H.; Barnard, D. L.; and Reist, E. J. *Nucleosides and Nucleotides*, 1989, 8, 833–836.
43. Still, W. C.; Hahn, M.; and Mitra, A. *J. Org. Chem.*, 1978, 43, 2923–2925.
44. R. A. Jones in "Oligonucleotide Synthesis: A Practical Approach," chapter 2, pp. 25–27, M. J. Gait (ed.), 1984, IRL Press Limited, Oxford.
45. R. A. Jones in "Oligonucleotide Synthesis: A Practical Approach," chapter 2, pp. 27–28, M. J. Gait (ed.), 1984, IRL Press Limited, Oxford.
46. Jones, G. H.; Hamamura, E. K.; and Moffatt, J. G. *Tetrahedron Lett.*, 1968, 55, 5731–34.
47. Cusack, N.J.; Reese, C. B.; Risius, A. C.; and Roozpeikar B. *Tetrahedron*, 1976, 32, 2157–62.
48. ElAmin, B.; Anantharamaiah, G. M.; Royer, G. P.; and Means, G. E. *J. Org. Chem.*, 1979, 44, 3442–3444.
49. Chu, C. K.; Matulic-Adamic, J.; Huang, J. -T.; Chou, T. -C.; Burchenal, J. H.; Fox, J. J.; and Watanabe, K. A. *Chem. Pharm. Bull.*, 1989, 37, 336–339.
50. Watanabe, K. A.; Reichman, U.; Hirota, K.; Lopez, C.; and Fox, J. J. *J. Med. Chem.*, 1979, 22, 21–24.
51. Tann, C. H.; Brodfuehrer, P. R.; Brundidge, S. P.; Sapino, Jr., C.; and Howell, H. G. *J. Org. Chem.*, 1985, 50, 3644–3647.
52. van de Sande, J. H.; Ramsing, N. B.; Germann, M. W.; Elhorst, W.; Kalisch, B. W.; Kitzing, E. V.; Pon, R. T.; Clegg, R. C.; and Jovin, T. M. *Science*, 1988, 241, 551–557.
53. T. Atkinson and M. Smith in "Oligonucleotide Synthesis: A Practical Approach," chapter 3, M. J. Gait (ed.), 1984, IRL Press Limited, Oxford.

What is claimed is:

1. A compound having the formula:

$$\underset{OR^2}{\underset{|}{R^2O-\overset{O}{\overset{\|}{P}}}}-CH_2CH_2-\underset{\underset{OH}{|}}{\overset{O}{\underset{F}{\bigcirc}}}-B$$

wherein:

B is adenosine, $N^6$-benzoyladenine, thymine, guanine, or $N^2$-isobutyrylguanine; and each $R^2$ is independently hydrogen, phenyl, alkyl (1–12C) or hydrogentriethylammonium ion.

2. The compound of claim 1 wherein B is guanine.
3. The compound of claim 2 wherein $R^2$ is hydrogen.
4. The compound of claim 3 wherein B is guanine.
5. The compound of claim 3 wherein B is $N^2$-isobutyrylguanine.
6. The compound of claim 3 wherein B is adenine.
7. The compound of claim 3 wherein B is $N^6$-benzoyladenine.
8. The compound of claim 3 wherein B is thymine.

* * * * *